United States Patent [19]

Misawa et al.

[11] Patent Number: 5,429,939
[45] Date of Patent: Jul. 4, 1995

[54] DNA SEQUENCES USEFUL FOR THE SYNTHESIS OF CAROTENOIDS

[75] Inventors: Norihiko Misawa; Kazuo Kobayashi; Katsumi Nakamura; Shigeyuki Yamano, all of Takasaki, Japan

[73] Assignee: Kirin Beer Kabushiki Kaisha, Tokyo, Japan

[21] Appl. No.: 783,705

[22] Filed: Oct. 23, 1991

Related U.S. Application Data

[63] Continuation-in-part of Ser. No. 519,011, Apr. 19, 1990, abandoned.

[30] Foreign Application Priority Data

Apr. 21, 1989 [JP] Japan .................................. 1-103078
Mar. 5, 1990 [JP] Japan .................................. 2-53255

[51] Int. Cl.$^6$ ............................................. C12P 23/00
[52] U.S. Cl. ..................... 435/67; 435/193; 435/189; 435/233; 435/69.1; 435/320.1; 435/252.3; 435/252.33; 435/75; 536/23.2; 536/23.1; 536/23.6; 935/14; 935/29; 935/60; 935/69; 935/73; 935/72; 930/240
[58] Field of Search ............... 435/67, 75, 69.1, 166, 435/167, 172.3, 320.1, 252.3, 252.33, 254, 255, 256, 847; 536/23.1, 23.2, 23.6; 585/351; 935/14; 800/205

[56] References Cited

PUBLICATIONS

Misawa et al. *Journal of Bacteriology* 172(12): 6704–6712 (Dec. 1990).
Ogura, K. *J. Biochem* 72: 1101–1108 (1972).
G. Thiry, J. Gen. Microbiology, 130, 1623–1631 (1984).
K. Perry, et al., J. of Bacteriology, 168(2), 607–612 (Nov. 1986).
R. W. Tuveson, et al. J. of Bacteriology, 170(10):4675–4680 (Oct. 1988).
G. A. Armstrong, et al., Mol. Gen. Genet 216: 254–268 (1989).
G. E. Bartley et al., J. of Biological Chemistry, 264(22):13109–13113 (1989).
Giuliano, G. et al. *Mol. Gen. Genet.* (1988) 213:78–83.
van der Krol, et al. 1990 The Plant Cell 2, 291–299.
Aragon et al, 1976. Eur. J. Biochem. 63, 71–75.
Berger et al (eds.) 1987. Methods in Enzymology 152, 33–110, 668, 669.

*Primary Examiner*—Christopher S. F. Low
*Attorney, Agent, or Firm*—Ladas & Parry

[57] ABSTRACT

Disclosed are DNA sequences which are useful for the synthesis of carotenoids such as lycopene, β-carotene, zeaxanthin or zeaxanthin-diglucoside, that is, DNA sequences encoding carotenoid biosynthesis enzymes. These DNA sequences are the sequences 1–6 shown in the specification.

Also disclosed is a process for producing a carotenoid or a carotenoid related compound which is selected from the group consisting of geranylgeranyl pyrophosphate, phytoene, lycopene, β-carotene, zeaxanthin and zeaxanthin-diglucoside, which comprises transforming a host with at least one of the DNA sequences 1–6 described above and culturing the transformant.

11 Claims, 9 Drawing Sheets

```
  1          10         20         30         40         50
GGTACCGCAC GGTCTGCCAA TCCGACGGAG GTTTATGAAT TTTCCACCTT TTCCACAAGC 70         80         90        100        110
TCAACTAGTA TTAACGATGT GGATTTAGCA AAAAAAACCT GTAACCCTAA ATGTAAAATA 130        140        150        160        170
ACGGGTAAGC CTGCCAACCA TGTTATGGCA GATTAAGCGT CTTTTTGAAG GGCACCGCAT 190        200        210        220    A   230
CTTTCGCGTT GCCGTAAATG TATCCGTTTA TAAGGACAGC CCGAATGACG GTCTGCGCAA 250        260        270        280        290
AAAAACACGT TCATCTCACT CGCGATGCTG CGGAGCAGTT ACTGGCTGAT ATTGATCGAC 310        320        330        340        350
GCCTTGATCA GTTATTGCCC GTGGAGGAG AACGGGATGT TGTGGGTGCC GCGATGCGTG 370        380        390        400        410
AAGGTGCGCT GGCACCGGGA AAACGTATTC GCCCCATGTT GCTGTTGCTG ACCGCCCGCG 430        440        450        460        470
ATCTGGGTTG CGCTGTCAGC CATGACGGAT TACTGGATTT GGCCTGTGCG GTGGAAATGG 490        500        510        520        530
TCCACGCGGC TTCGCTGATC CTTGACGATA TGCCCTGCAT GGACGATGCG AAGCTGCGGC 550        560        570        580        590
GCGGACGCCC TACCATTCAT TCTCATTACG GAGAGCATGT GGCAATACTG GCGGCGGTTG 610        620        630        640        650
CCTTGCTGAG TAAAGCCTTT GGCGTAATTG CCGATGCAGA TGGCCTCACG CCGCTGGCAA 670        680        690        700        710
AAAATCGGGC GGTTTCTGAA CTGTCAAACG CCATCGGCAT GCAAGGATTG GTTCAGGGTC 730        740        750        760        770
AGTTCAAGGA TCTGTCTGAA GGGGATAAGC CGCGCAGCGC TGAAGCTATT TTGATGACGA 790        800        810        820        830
ATCACTTTAA AACCAGCACG CTGTTTTGTG CCTCCATGCA GATGGCCTCG ATTGTTGCGA 850        860        870        880        890
ATGCCTCCAG CGAAGCGCGT GATTGCCTGC ATCGTTTTTC ACTTGATCTT GGTCAGGCAT 910        920        930        940        950
TTCAACTGCT GGACGATTTG ACCGATGGCA TGACCGACAC CGGTAAGGAT AGCAATCAGG 970        980        990       1000       1010
ACGCCGGTAA ATCGACGCTG GTCAATCTGT TAGGCCCGAG GGCGGTTGAA GAACGTCTGA 1030       1040       1050       1060       1070
GACAACATCT TCAGCTTGCC AGTGAGCATC TCTCTGCGGC CTGCCAACAC GGGCACGCCA 1090       1100       1110       1120       1130 B
CTCAACATTT TATTCAGGCC TGGTTTGACA AAAAACTCGC TGCCGTCAGT TAAGGATGCT
```

FIG. I(a)

```
       C   1150        1160       1170        1180       1190
       |
       GCATGAGCCA TTTCGCGGCG ATCGCACCGC CTTTTTACAG CCATGTTCGC GCATTACAGA 1210        1220       1230        1240       1250
       ATCTCGCTCA GGAACTGGTC GCGCGCGGTC ATCGGGTGAC CTTTATTCAG CAATACGATA 1270        1280       1290        1300       1310
       TTAAACACTT GATCGATAGC GAAACCATTG GATTTCATTC CGTCGGACA  GACAGCCATC 1330        1340       1350        1360       1370
       CCCCCGGCGC GTTAACGCGC GTGCTACACC TGGCGGCTCA TCCTCTGGGG CCGTCAATGC 1390        1400       1410        1420       1430
       TGAAGCTCAT CAATGAAATG GCGCGCACCA CCGATATGCT GTGCCGCGAA CTCCCCCAGG 1450        1460       1470        1480       1490
       CATTTAACGA TCTGGCCGTC GATGGCGTCA TTGTTGATCA AATGGAACCG GCAGGCGCGC 1510        1520       1530        1540       1550
       TCGTTGCTGA AGCACTGGGA CTGCCGTTTA TCTCTGTCGC CTGCGCGCTG CCTCTCAATC 1570        1580       1590        1600       1610
       GTGAACCGGA TATGCCCCTG GCGGTTATGC CTTTCGAATA CGGGACCAGC GACGCGGCTC 1630        1640       1650        1660       1670
       GCGAACGTTA TGCCGCCAGT GAAAAAATTT ATGACTGGCT AATGCGTCGT CATGACCGTG 1690        1700       1710        1720       1730
       TCATTGCCGA ACACAGCCAC AGAATGGGCT TAGCCCCCCG GCAAAAGCTT CACCAGTGTT 1750        1760       1770        1780       1790
       TTTCGCCACT GGCGCAAATC AGCCAGCTTG TTCCTGAACT GGATTTTCCC CGCAAAGCGT 1810        1820       1830        1840       1850
       TACCGGCTTG TTTTCATGCC GTCGGGCCTC TGCGCGAAAC GCACGCACCG TCAACGTCTT 1870        1880       1890        1900       1910
       CATCCCGTTA TTTTACATCC TCAGAAAAAC CCCGGATTTT CGCCTCGCTG GCACGCTTC 1930        1940       1950        1960       1970
       AGGGACACCG TTATGGGCTG TTTAAAACGA TAGTGAAAGC CTGTGAAGAA ATTGACGGTC 1990        2000       2010        2020       2030
       AGCTCCTGTT AGCCCACTGT GGTCGTCTTA CGGACTCTCA GTGTGAAGAG CTGGCGCGAA 2050        2060       2070        2080       2090
       GCCGTCATAC ACAGGTGGTG GATTTGCCG  ATCAGTCAGC CGCGCTGTCT CAGGCGCAGC 2110        2120       2130        2140       2150
       TGGCGATCAC CCACGGCGGC ATGAATACGG TACTGGACGC GATTAATTAC CGGACGCCCC 2170        2180       2190        2200       2210
       TTTTAGCGCT TCCGCTGGCC TTTGATCAGC CCGGCGTCGC GTCACGCATC GTTTATCACG 2230        2240       2250        2260       2270
       GCATCGGCAA GCGTGCTTCC CGCTTTACCA CCAGCCATGC TTTGGCTCGT CAGATGCGTT
```

FIG. 1(b)

```
          2290       2300       2310       2320       2330
     CATTGCTGAC CAACGTCGAC TTTCAGCAGC GCATGGCGAA AATCCAGACA GCCCTTCGTT 2350       2360       2370       2380       2390
     TGGCAGGGGG CACCATGGCC GCTGCCGATA TCATTGAGCA GGTTATGTGC ACCGGTCAGC 2410       2420    E  2430     D  2440      2450
     CTGTCTTAAG TGGGAGCGGC TATGCAACCG CATTATGATC TGATTCTCGT GGGGGCTGGA 2470       2480       2490       2500       2510
     CTCGCGAATG GCCTTATCGC CCTGCGTCTT CAGCAGCAGC AACCTGATAT GCGTATTTTG 2530       2540       2550       2560       2570
     CTTATCGACG CCGCACCCCA GGCGGGCGGG AATCATACGT GGTCATTTCA CCACGATGAT 2590       2600       2610       2620       2630
     TTGACTGAGA GCCAACATCG TTGGATAGCT CCGCTGGTGG TTCATCACTG GCCCGACTAT 2650       2660       2670       2680       2690
     CAGGTACGCT TTCCCACACG CCGTCGTAAG CTGAACAGCG GCTACTTTTG TATTACTTCT 2710       2720       2730       2740       2750
     CAGCGTTTCG CTGAGGTTTT ACAGCGACAG TTTGGCCCGC ACTTGTGGAT GGATACCGCG 2770       2780       2790       2800       2810
     GTCGCAGAGG TTAATGCGGA ATCTGTTCGG TTGAAAAAGG GTCAGGTTAT CGGTGCCCGC 2830       2840       2850       2860       2870
     GCGGTGATTG ACGGGCGGGG TTATGCGGCA AATTCAGCAC TGAGCGTGGG CTTCCAGGCG 2890       2900       2910       2920       2930
     TTTATTGGCC AGGAATGGCG ATTGAGCCAC CCGCATGGTT TATCGTCTCC CATTATCATG 2950       2960       2970       2980       2990
     GATGCCACGG TCGATCAGCA AAATGGTTAT CGCTTCGTGT ACAGCCTGCC GCTCTCGCCG 3010       3020       3030       3040       3050
     ACCAGATTGT TAATTGAAGA CACGCACTAT ATTGATAATG CGACATTAGA TCCTGAATGC 3070       3080       3090       3100       3110
     GCGCGGCAAA ATATTTGCGA CTATGCCGCG CAACAGGGTT GGCAGCTTCA GACACTGCTG 3130       3140       3150       3160       3170
     CGAGAAGAAC AGGGCGCCTT ACCCATTACT CTGTCGGGCA ATGCCGACGC ATTCTGGCAG 3190       3200       3210       3220       3230
     CAGCGCCCCC TGGCCTGTAG TGGATTACGT GCCGGTCTGT TCCATCCTAC CACCGGCTAT 3250       3260       3270       3280       3290
     TCACTGCCGC TGGCGGTTGC CGTGGCCGAC CGCCTGAGTG CACTTGATGT CTTTACGTCG 3310       3320       3330       3340       3350
     GCCTCAATTC ACCATGCCAT TACGCATTTT GCCCGCGAGC GCTGGCAGCA GCAGGGCTTT 3370       3380       3390       3400       3410
     TTCCGCATGC TGAATCGCAT GCTGTTTTTA GCCGGACCCG CCGATTCACG CTGGCGGGTT
```

FIG. 1(c)

```
       4570       4580       4590       4600       4610
  TCGGCCCGCG TTACCGCGAG CTGATTGACG AAATTTTTAA TCATGATGGC CTCGCAGAGG 4630       4640       4650       4660       4670
  ACTTCTCACT TTATCTGCAC GCGCCCTGTG TCACGGATTC GTCACTGGCG CCTGAAGGTT 4690       4700       4710       4720       4730
  GCGGCAGTTA CTATGTGTTG GCGCCGGTGC CGCATTTAGG CACCGCGAAC CTCGACTGGA 4750       4760       4770       4780       4790
  CGGTTGAGGG GCCAAAACTA CGCGACCGTA TTTTTGCGTA CCTTGAGCAG CATTACATGC 4810       4820       4830       4840       4850
  CTGGCTTACG GAGTCAGCTG GTCACGCACC GGATGTTTAC GCCGTTTGAT TTTCGCGACC 4870       4880       4890       4900       4910
  AGCTTAATGC CTATCATGGC TCAGCCTTTT CTGTGGAGCC CGTTCTTACC CAGAGCGCCT 4930       4940       4950       4960       4970
  GGTTTCGGCC GCATAACCGC GATAAAACCA TTACTAATCT CTACCTGGTC GGCGCAGGCA 4990       5000       5010       5020       5030
  CGCATCCCGG CGCAGGCATT CCTGGCGTCA TCGGCTCGGC AAAAGCGACA GCAGGTTTGA 5050       5060       5070       5080       5090
  TGCTGGAGGA TCT ATTTGA ATAATCCGTC GTTACTCAAT CATGCGGTCG AAACGATGGC 5110       5120       5130       5140       5150
  AGTTGGCTCG AAAAGTTTTG CGACAGCCTC AAAGTTATTT GATGCAAAAA CCCGGCGCAG 5170       5180       5190       5200       5210
  CGTACTGATG CTCTACGCCT GGTGCCGCCA TTGTGACGAT GTTATTGACG ATCAGACGCT 5230       5240       5250       5260       5270
  GGGCTTTCAG GCCCGGCAGC CTGCCTTACA AACGCCCGAA CAACGTCTGA TGCAACTTGA 5290       5300       5310       5320       5330
  GATGAAAACG CGCCAGGCCT ATGCAGGATC GCAGATGCAC GAACCGGCGT TTGCGGCTTT 5350       5360       5370       5380       5390
  TCAGGAAGTG GCTATGGCTC ATGATATCGC CCCGGCTTAC GCGTTTGATC ATCTGGAAGG 5410       5420       5430       5440       5450
  CTTCGCCATG GATGTACGCG AAGCGCAATA CAGCCAACTG GATGATACGC TGCGCTATTG 5470       5480       5490       5500       5510
  CTATCACGTT GCAGGCGTTG TCGGCTTGAT GATGGCGCAA ATCATGGGCG TGCGGGATAA 5530       5540       5550       5560       5570
  CGCCACGCTG GACCGCGCCT GTGACCTTGG GCTGGCATTT CAGTTGACCA ATATTGCTCG 5590       5600       5610       5620       5630
  CGATATTGTG GACGATGCGC ATGCGGGCCG CTGTTATCTG CCGGCAAGCT GGCTGGAGCA 5650       5660       5670       5680       5690
  TGAAGGTCTG AACAAAGAGA ATTATGCGGC ACCTGAAAAC CGTCAGGCGC TGAGCCGTAT
```

FIG. 1(e)

```
      4570       4580       4590       4600       4610
TCGGCCCGCG TTACCGCGAG CTGATTGACG AAATTTTTAA TCATGATGGC CTCGCAGAGG 4630       4640       4650       4660       4670
ACTTCTCACT TTATCTGCAC GCGCCCTGTG TCACGGATTC GTCACTGGCG CCTGAAGGTT 4690       4700       4710       4720       4730
GCGGCAGTTA CTATGTGTTG GCGCCGGTGC CGCATTTAGG CACCGCGAAC CTCGACTGGA 4750       4760       4770       4780       4790
CGGTTGAGGG GCCAAAACTA CGCGACCGTA TTTTTGCGTA CCTTGAGCAG CATTACATGC 4810       4820       4830       4840       4850
CTGGCTTACG GAGTCAGCTG GTCACGCACC GGATGTTTAC GCCGTTTGAT TTTCGCGACC 4870       4880       4890       4900       4910
AGCTTAATGC CTATCATGGC TCAGCCTTTT CTGTGGAGCC CGTTCTTACC CAGAGCGCCT 4930       4940       4950       4960       4970
GGTTTCGGCC GCATAACCGC GATAAAACCA TTACTAATCT CTACCTGGTC GGCGCAGGCA 4990       5000       5010       5020       5030
CGCATCCCGG CGCAGGCATT CCTGGCGTCA TCGGCTCGGC AAAAGCGACA GCAGGTTTGA
                H
      5050       5060       5070       5080       5090
TGCTGGAGGA TCT ATTTGA ATAATCCGTC GTTACTCAAT CATGCGGTCG AAACGATGGC 5110       5120       5130       5140       5150
AGTTGGCTCG AAAAGTTTTG CGACAGCCTC AAAGTTATTT GATGCAAAAA CCCGGCGCAG 5170       5180       5190       5200       5210
CGTACTGATG CTCTACGCCT GGTGCCGCCA TTGTGACGAT GTTATTGACG ATCAGACGCT 5230       5240       5250       5260       5270
GGGCTTTCAG GCCCGGCAGC CTGCCTTACA AACGCCCGAA CAACGTCTGA TGCAACTTGA 5290       5300       5310       5320       5330
GATGAAAACG CGCCAGGCCT ATGCAGGATC GCAGATGCAC GAACCGGCGT TTGCGGCTTT 5350       5360       5370       5380       5390
TCAGGAAGTG GCTATGGCTC ATGATATCGC CCCGGCTTAC GCGTTTGATC ATCTGGAAGG 5410       5420       5430       5440       5450
CTTCGCCATG GATGTACGCG AAGCGCAATA CAGCCAACTG GATGATACGC TGCGCTATTG 5470       5480       5490       5500       5510
CTATCACGTT GCAGGCGTTG TCGGCTTGAT GATGGCGCAA ATCATGGGCG TGCGGGATAA 5530       5540       5550       5560       5570
CGCCACGCTG GACCGCGCCT GTGACCTTGG GCTGGCATTT CAGTTGACCA ATATTGCTCG 5590       5600       5610       5620       5630
CGATATTGTG GACGATGCGC ATGCGGGCCG CTGTTATCTG CCGGCAAGCT GGCTGGAGCA 5650       5660       5670       5680       5690
TGAAGGTCTG AACAAAGAGA ATTATGCGGC ACCTGAAAAC CGTCAGGCGC TGAGCCGTAT
```

FIG. 1(e)

```
       5710       5720       5730       5740       5750
  CGCCCGTCGT TTGGTGCAGG AAGCAGAACC TTACTATTTG TCTGCCACAG CCGGCCTGGC 5770       5780       5790       5800       5810
  AGGGTTGCCC CTGCGTTCCG CCTGGGCAAT CGCTACGGCG AAGCAGGTTT ACCGGAAAAT 5830       5840       5850       5860       5870
  AGGTGTCAAA GTTGACAGG CCGGTCAGCA AGCCTGGGAT CAGCGGCAGT CAACGACCAC
                                                         L
       5890       5900       5910       5920       5930
  GCCCGAAAAA TTAACGCTGC TGCTGGCCGC CTCTGGTCAG GCCCTTACTT CCCGGATGCG 5950       5960       5970       5980     J 5990
  GGCTCATCCT CCCCGCCCTG CGCATCTCTG GCAGCGCCCG CTCTAGCGCC ATGTCTTTCC 6010       6020       6030       6040       6050
  CGGAGCGTCG CCTGAAGTTT TGACAGGGGC GGCGCATAGA GGAAGCCAAA AGAAACACAA 6070       6080       6090       6100       6110
  CCTTCTTTGC CCCTGACGGC GTGATGCATA CGGTGCGCCA TATACAACCG TTTGAGGTAG 6130       6140       6150       6160       6170
  CCCTTGCGTG GAATATAGCG GAATGGCCAA CGTTGATGCA CCAGCCCGTC GTGCACCATA 6190       6200       6210       6220       6230
  AAATAGAGTA ATCCATACGC CGTCATACCT GCGCCAATCC ACTGGAGCGG CCACATTCCT 6250       6260       6270       6280       6290
  GTACTGCCCA GATAAATCAG CAGGATCGAT AATGCAGCAA AAACCACGGC ATAAAGATCG 6310       6320       6330       6340       6350
  TTAACTTCAA ACGCACCTTT ACGCGGTTCA TGATGTGAAA GATGCCATCC CCAACCCCAG 6370       6380       6390       6400       6410
  CCGTGCATGA TGTATTTGTG TGCCAGTGCA GCAATCACTT CCATGCCAAT CACGGTAACG 6430       6440       6450   K   6460       6470
  AAAACGATCA GGGCATTCCA AATCCACAAC ATAATTTCTC CGGTAGAGAC GTCTGGCAGC 6490       6500       6510       6520       6530
  AGGCTTAAGG ATTCAATTTT AACAGAGATT AGCCGATCTG GCGGCGGGAA GGGAAAAAGG 6550       6560       6570       6580       6590
  CGCGCCAGAA AGGCGCGCCA GGGATCAGAA GTCGGCTTTC AGAACCACAC GGTAGTTGGC 6610       6620       6630       6640       6650
  TTTACCTGCA CGAACATGGT CCAGTGCATC GTTGATTTTC GACATCGGGA AGTACTCCAC 6670       6680       6690       6700       6710
  TGTCGGCGCA ATATCTGTAC GGCCAGCCAG CTTCAGCAGT GAACGCAGCT GCGCAGGTGA 6730       6740       6750       6760       6770
  ACCGGTTGAA GAACCCGTCA CGGCGCGGTC GCCTAAAATC AGGCTGAAAG CCGGGCACGT 6790       6800       6810       6820       6830
  CAAACGGCTT CAGTACGGCA CCCACGGTAT GGAACTTACC GCGAGGCGCC AGGGCCGCAA
```

FIG. 1(f)

```
       6850       6860       6870       6880       6890
AGTAGGGTTG CCAGTCGAGA TCGACGGCGA CCGTGCTGAT AATCAGGTCA AACTGGCCCG 6910       6918
CCAGGCTTTT TAAAGCTT
```

FIG. I (g)

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
      ( A ) LENGTH: 302 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

| | | | | | | | | | | | | | | |
|---|---|---|---|---|---|---|---|---|---|---|---|---|---|---|
| Met<br>1 | Thr | Val | Cys | Ala<br>5 | Lys | Lys | His | Val | Leu<br>10 | Thr | Arg | Asp | Ala<br>15 | Ala |
| Glu | Gln | Leu | Leu<br>20 | Ala | Asp | Ile | Asp | Arg<br>25 | Arg | Leu | Asp | Gln | Leu<br>30 | Leu | Pro |
| Val | Glu | Gly<br>35 | Glu | Arg | Asp | Val<br>40 | Val | Gly | Ala | Ala | Met<br>45 | Arg | Glu | Gly | Ala |
| Leu | Ala<br>50 | Pro | Gly | Lys | Arg | Ile<br>55 | Arg | Pro | Met | Leu | Leu<br>60 | Leu | Leu | Thr | Ala |
| Arg<br>65 | Asp | Leu | Gly | Cys<br>70 | Ala | Val | Ser | His | Asp<br>75 | Gly | Leu | Leu | Asp | Leu<br>80 | Ala |
| Cys | Ala | Val | Glu | Met<br>85 | Val | His | Ala | Ala | Ser<br>90 | Leu | Ile | Leu | Asp | Asp<br>95 | Met |
| Pro | Cys | Met | Asp<br>100 | Asp | Ala | Lys | Leu | Arg<br>105 | Arg | Gly | Arg | Pro | Thr<br>110 | Ile | His |
| Ser | His | Tyr<br>115 | Gly | Glu | His | Val<br>120 | Ala | Ile | Leu | Ala | Ala<br>125 | Val | Ala | Leu | Leu |
| Ser | Lys<br>130 | Ala | Phe | Gly | Val<br>135 | Ile | Ala | Asp | Ala | Asp<br>140 | Gly | Leu | Thr | Pro | Leu |
| Ala<br>145 | Lys | Asn | Arg | Ala<br>150 | Val | Ser | Glu | Leu | Ser<br>155 | Asn | Ala | Ile | Gly | Met<br>160 | Gln |
| Gly | Leu | Val | Gln<br>165 | Gly | Gln | Phe | Lys | Asp<br>170 | Leu | Ser | Glu | Gly | Asp<br>175 | Lys | Pro |
| Arg | Ser | Ala | Glu<br>180 | Ala | Ile | Leu | Met | Thr<br>185 | Asn | His | Phe | Lys | Thr<br>190 | Ser | Thr |
| Leu | Phe | Cys<br>195 | Ala | Ser | Met | Gln | Met<br>200 | Ala | Ser | Ile | Val | Ala<br>205 | Asn | Ala | Ser |
| Ser | Glu<br>210 | Ala | Arg | Asp | Cys | Leu<br>215 | His | Arg | Phe | Ser | Leu<br>220 | Asp | Leu | Gly | Gln |
| Ala<br>225 | Phe | Gln | Leu | Leu | Asp<br>230 | Asp | Leu | Thr | Asp | Gly<br>235 | Met | Thr | Asp | Thr | Gly<br>240 |
| Lys | Asp | Ser | Asn | Gln<br>245 | Asp | Ala | Gly | Lys | Ser<br>250 | Thr | Leu | Val | Asn | Leu<br>255 | Leu |
| Gly | Pro | Arg | Ala<br>260 | Val | Glu | Glu | Arg | Leu<br>265 | Arg | Gln | His | Leu | Gln<br>270 | Leu | Ala |
| Ser | Glu | His<br>275 | Leu | Ser | Ala | Ala | Cys<br>280 | Gln | His | Gly | His | Ala<br>285 | Thr | Gln | His |
| Phe | Ile<br>290 | Gln | Ala | Trp | Phe | Asp<br>295 | Lys | Lys | Leu | Ala | Ala<br>300 | Val | Ser | | |

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met<br>1 | Ser | His | Phe | Ala<br>5 | Ala | Ile | Ala | Pro | Pro<br>10 | Phe | Tyr | Ser | His | Val<br>15 | Arg |
| Ala | Leu | Gln | Asn<br>20 | Leu | Ala | Gln | Glu | Leu<br>25 | Val | Ala | Arg | Gly | His<br>30 | Arg | Val |
| Thr | Phe | Ile<br>35 | Gln | Gln | Tyr | Asp | Ile<br>40 | Lys | His | Leu | Ile | Asp<br>45 | Ser | Glu | Thr |
| Ile | Gly<br>50 | Phe | His | Ser | Val | Gly<br>55 | Thr | Asp | Ser | His | Pro<br>60 | Pro | Gly | Ala | Leu |
| Thr | Arg | Val | Leu | His | Leu | Ala | Ala | His | Pro | Leu | Gly | Pro | Ser | Met | Leu |

-continued

|  | 65 |  |  |  |  | 70 |  |  |  |  | 75 |  |  |  |  | 80 |
|---|---|---|---|---|---|---|---|---|---|---|---|---|---|---|---|---|

Lys Leu Ile Asn Glu Met Ala Arg Thr Thr Asp Met Leu Cys Arg Glu
        85       90       95

Leu Pro Gln Ala Phe Asn Asp Leu Ala Val Asp Gly Val Ile Val Asp
    100       105       110

Gln Met Glu Pro Ala Gly Ala Leu Val Ala Glu Ala Leu Gly Leu Pro
    115       120       125

Phe Ile Ser Val Ala Cys Ala Leu Pro Leu Asn Arg Glu Pro Asp Met
 130       135       140

Pro Leu Ala Val Met Pro Phe Glu Tyr Gly Thr Ser Asp Ala Ala Arg
145       150       155      160

Glu Arg Tyr Ala Ala Ser Glu Lys Ile Tyr Asp Trp Leu Met Arg Arg
    165       170       175

His Asp Arg Val Ile Ala Glu His Ser His Arg Met Gly Leu Ala Pro
    180       185       190

Arg Gln Lys Leu His Gln Cys Phe Ser Pro Leu Ala Gln Ile Ser Gln
   195       200       205

Leu Val Pro Glu Leu Asp Phe Pro Arg Lys Ala Leu Pro Ala Cys Phe
  210       215       220

His Ala Val Gly Pro Leu Arg Glu Thr His Ala Pro Ser Thr Ser Ser
225       230       235      240

Ser Arg Tyr Phe Thr Ser Ser Glu Lys Pro Arg Ile Phe Ala Ser Leu
    245       250       255

Gly Thr Leu Gln Gly His Arg Tyr Gly Leu Phe Lys Thr Ile Val Lys
   260       265       270

Ala Cys Glu Glu Ile Asp Gly Gln Leu Leu Leu Ala His Cys Gly Arg
   275       280       285

Leu Thr Asp Ser Gln Cys Glu Glu Leu Ala Arg Ser Arg His Thr Gln
  290       295       300

Val Val Asp Phe Ala Asp Gln Ser Ala Ala Leu Ser Gln Ala Gln Leu
305       310       315      320

Ala Ile Thr His Gly Gly Met Asn Thr Val Leu Asp Ala Ile Asn Tyr
    325       330       335

Arg Thr Pro Leu Leu Ala Leu Pro Leu Ala Phe Asp Gln Pro Gly Val
   340       345       350

Ala Ser Arg Ile Val Tyr His Gly Ile Gly Lys Arg Ala Ser Arg Phe
   355       360       365

Thr Thr Ser His Ala Leu Ala Arg Gln Met Arg Ser Leu Leu Thr Asn
  370       375       380

Val Asp Phe Gln Gln Arg Met Ala Lys Ile Gln Thr Ala Leu Arg Leu
385       390       395      400

Ala Gly Gly Thr Met Ala Ala Ala Asp Ile Ile Glu Gln Val Met Cys
    405       410       415

Thr Gly Gln Pro Val Leu Ser Gly Ser Gly Tyr Ala Thr Ala Leu
   420       425       430

( 2 ) INFORMATION FOR SEQ ID NO:3:

( i ) SEQUENCE CHARACTERISTICS:
    ( A ) LENGTH: 382 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

Met Gln Pro His Tyr Asp Leu Ile Leu Val Gly Ala Gly Leu Ala Asn
1       5       10       15

| | | | | | | | | | | | | |
|---|---|---|---|---|---|---|---|---|---|---|---|---|
| Gly | Leu | Ile | Ala | Leu | Arg | Leu | Gln | Gln | Gln | Pro | Asp | Met | Arg | Ile |
| | | 20 | | | | | 25 | | | | 30 | | |
| Leu | Leu | Ile | Asp | Ala | Ala | Pro | Gln | Ala | Gly | Gly | Asn | His | Thr | Trp | Ser |
| | | 35 | | | | 40 | | | | | 45 | | | |
| Phe | His | His | Asp | Asp | Leu | Thr | Glu | Ser | Gln | His | Arg | Trp | Ile | Ala | Pro |
| | 50 | | | | 55 | | | | | 60 | | | | |
| Leu | Val | Val | His | His | Trp | Pro | Asp | Tyr | Gln | Val | Arg | Phe | Pro | Thr | Arg |
| 65 | | | | 70 | | | | | 75 | | | | | 80 |
| Arg | Arg | Lys | Leu | Asn | Ser | Gly | Tyr | Phe | Cys | Ile | Thr | Ser | Gln | Arg | Phe |
| | | | 85 | | | | | 90 | | | | | 95 | |
| Ala | Glu | Val | Leu | Gln | Arg | Gln | Phe | Gly | Pro | His | Leu | Trp | Met | Asp | Thr |
| | | 100 | | | | | 105 | | | | 110 | | | |
| Ala | Val | Ala | Glu | Val | Asn | Ala | Glu | Ser | Val | Arg | Leu | Lys | Lys | Gly | Gln |
| | 115 | | | | | 120 | | | | | 125 | | | | |
| Val | Ile | Gly | Ala | Arg | Ala | Val | Ile | Asp | Gly | Arg | Gly | Tyr | Ala | Ala | Asn |
| 130 | | | | | 135 | | | | | 140 | | | | | |
| Ser | Ala | Leu | Ser | Val | Gly | Phe | Gln | Ala | Phe | Ile | Gly | Gln | Glu | Trp | Arg |
| 145 | | | | 150 | | | | | 155 | | | | | 160 | |
| Leu | Ser | His | Pro | His | Gly | Leu | Ser | Ser | Pro | Ile | Ile | Met | Asp | Ala | Thr |
| | | | 165 | | | | | 170 | | | | 175 | | | |
| Val | Asp | Gln | Gln | Asn | Gly | Tyr | Arg | Phe | Val | Tyr | Ser | Leu | Pro | Leu | Ser |
| | | 180 | | | | | 185 | | | | 190 | | | | |
| Pro | Thr | Arg | Leu | Leu | Ile | Glu | Asp | Thr | His | Tyr | Ile | Asp | Asn | Ala | Thr |
| | 195 | | | | | 200 | | | | 205 | | | | | |
| Leu | Asp | Pro | Glu | Cys | Ala | Arg | Gln | Asn | Ile | Cys | Asp | Tyr | Ala | Ala | Gln |
| 210 | | | | | 215 | | | | 220 | | | | | | |
| Gln | Gly | Trp | Gln | Leu | Gln | Thr | Leu | Leu | Arg | Glu | Glu | Gln | Gly | Ala | Leu |
| 225 | | | | | 230 | | | | 235 | | | | | 240 | |
| Pro | Ile | Thr | Leu | Ser | Gly | Asn | Ala | Asp | Ala | Phe | Trp | Gln | Gln | Arg | Pro |
| | | | 245 | | | | 250 | | | | 255 | | | | |
| Leu | Ala | Cys | Ser | Gly | Leu | Arg | Ala | Gly | Leu | Phe | His | Pro | Thr | Thr | Gly |
| | | 260 | | | | | 265 | | | | 270 | | | | |
| Tyr | Ser | Leu | Pro | Leu | Ala | Val | Ala | Val | Ala | Asp | Arg | Leu | Ser | Ala | Leu |
| | 275 | | | | 280 | | | | | 285 | | | | | |
| Asp | Val | Phe | Thr | Ser | Ala | Ser | Ile | His | His | Ala | Ile | Thr | His | Phe | Ala |
| 290 | | | | | 295 | | | | 300 | | | | | | |
| Arg | Glu | Arg | Trp | Gln | Gln | Gln | Gly | Phe | Phe | Arg | Met | Leu | Asn | Arg | Met |
| 305 | | | | 310 | | | | | 315 | | | | | 320 | |
| Leu | Phe | Leu | Ala | Gly | Pro | Ala | Asp | Ser | Arg | Trp | Arg | Val | Met | Gln | Arg |
| | | | 325 | | | | | 330 | | | | 335 | | | |
| Phe | Tyr | Gly | Leu | Pro | Glu | Asp | Leu | Ile | Ala | Arg | Phe | Tyr | Ala | Gly | Lys |
| | | 340 | | | | | 345 | | | | 350 | | | | |
| Leu | Thr | Leu | Thr | Asp | Arg | Leu | Arg | Ile | Leu | Ser | Gly | Lys | Pro | Pro | Val |
| | 355 | | | | | 360 | | | | 365 | | | | | |
| Pro | Val | Leu | Ala | Ala | Leu | Gln | Ala | Ile | Met | Thr | Thr | His | Arg | | |
| 370 | | | | | 375 | | | | | 380 | | | | | |

(2) INFORMATION FOR SEQ ID NO:4:

(i) SEQUENCE CHARACTERISTICS:
        (A) LENGTH: 492 amino acids
        (B) TYPE: amino acid
        (D) TOPOLOGY: linear (ii) MOLECULE TYPE: protein (xi) SEQUENCE DESCRIPTION: SEQ ID NO:4:

-continued

| | | | | | | | | | | | | | | |
|---|---|---|---|---|---|---|---|---|---|---|---|---|---|---|
| Met 1 | Lys | Pro | Thr | Thr 5 | Val | Ile | Gly | Ala | Gly 10 | Phe | Gly | Gly | Leu | Ala Leu 15 |
| Ala | Ile | Arg | Leu 20 | Gln | Ala | Ala | Gly | Ile 25 | Pro | Val | Leu | Leu | Leu 30 | Glu Gln |
| Arg | Asp | Lys 35 | Pro | Gly | Gly | Arg | Ala 40 | Tyr | Val | Tyr | Glu | Asp 45 | Gln | Gly Phe |
| Thr | Phe 50 | Asp | Ala | Gly | Pro | Thr 55 | Val | Ile | Thr | Asp | Pro 60 | Ser | Ala | Ile Glu |
| Glu 65 | Leu | Phe | Ala | Leu | Ala 70 | Gly | Lys | Gln | Leu | Lys 75 | Glu | Tyr | Val | Glu Leu 80 |
| Leu | Pro | Val | Thr | Pro 85 | Phe | Tyr | Arg | Leu | Cys 90 | Trp | Glu | Ser | Gly | Lys Val 95 |
| Phe | Asn | Tyr | Asp 100 | Asn | Asp | Gln | Thr | Arg 105 | Leu | Glu | Ala | Gln | Ile 110 | Gln Gln |
| Phe | Asn | Pro 115 | Arg | Asp | Val | Glu | Gly 120 | Tyr | Arg | Gln | Phe | Leu 125 | Asp | Tyr Ser |
| Arg | Ala 130 | Val | Phe | Lys | Glu | Gly 135 | Tyr | Leu | Lys | Leu | Gly 140 | Thr | Val | Pro Phe |
| Leu 145 | Ser | Phe | Arg | Asp | Met 150 | Leu | Arg | Ala | Ala | Pro 155 | Gln | Leu | Ala | Lys Leu 160 |
| Gln | Ala | Trp | Arg | Ser 165 | Val | Tyr | Ser | Lys | Val 170 | Ala | Ser | Tyr | Ile 175 | Glu Asp |
| Glu | His | Leu | Arg 180 | Gln | Ala | Phe | Ser | Phe 185 | His | Ser | Leu | Leu | Val 190 | Gly Gly |
| Asn | Pro | Phe 195 | Ala | Thr | Ser | Ser | Ile 200 | Tyr | Thr | Leu | Ile | His 205 | Ala | Leu Glu |
| Arg | Glu 210 | Trp | Gly | Val | Trp | Phe 215 | Pro | Arg | Gly | Gly | Thr 220 | Gly | Ala | Leu Val |
| Gln 225 | Gly | Met | Ile | Lys | Leu 230 | Phe | Gln | Asp | Leu | Gly 235 | Gly | Glu | Val | Val Leu 240 |
| Asn | Ala | Arg | Val | Ser 245 | His | Met | Glu | Thr | Thr 250 | Gly | Asn | Lys | Ile | Glu Ala 255 |
| Val | His | Leu | Glu 260 | Asp | Gly | Arg | Arg | Phe 265 | Leu | Thr | Gln | Ala | Val 270 | Ala Ser |
| Asn | Ala | Asp 275 | Val | Val | His | Thr | Tyr 280 | Arg | Asp | Leu | Leu | Ser 285 | Gln | His Pro |
| Ala | Ala 290 | Val | Lys | Gln | Ser | Asn 295 | Lys | Leu | Gln | Thr | Lys 300 | Arg | Met | Ser Asn |
| Ser 305 | Leu | Phe | Val | Leu | Tyr 310 | Phe | Gly | Leu | Asn | His 315 | His | Asp | Gln | Leu 320 |
| Ala | His | His | Thr | Val 325 | Cys | Phe | Gly | Pro | Arg 330 | Tyr | Arg | Glu | Leu | Ile Asp 335 |
| Glu | Ile | Phe | Asn 340 | His | Asp | Gly | Leu | Ala 345 | Glu | Asp | Phe | Ser | Leu 350 | Tyr Leu |
| His | Ala | Pro 355 | Cys | Val | Thr | Asp | Ser 360 | Ser | Leu | Ala | Pro | Glu 365 | Gly | Cys Gly |
| Ser | Tyr 370 | Tyr | Val | Leu | Ala | Pro 375 | Val | Pro | His | Leu | Gly 380 | Thr | Ala | Asn Leu |
| Asp 385 | Trp | Thr | Val | Glu | Gly 390 | Pro | Lys | Leu | Arg | Asp 395 | Arg | Ile | Phe | Ala Tyr 400 |
| Leu | Glu | Gln | His | Tyr 405 | Met | Pro | Gly | Leu | Arg 410 | Ser | Gln | Leu | Val | Thr His 415 |
| Arg | Met | Phe | Thr 420 | Pro | Phe | Asp | Phe | Arg 425 | Asp | Gln | Leu | Asn | Ala 430 | Tyr His |
| Gly | Ser | Ala | Phe | Ser | Val | Glu | Pro | Val | Leu | Thr | Gln | Ser | Ala | Trp Phe |

```
                    435                     440                     445
Arg Pro His Asn Arg Asp Lys Thr Ile Thr Asn Leu Tyr Leu Val Gly
    450                     455                     460

Ala Gly Thr His Pro Gly Ala Gly Ile Pro Gly Val Ile Gly Ser Ala
465                     470                     475                 480

Lys Ala Thr Ala Gly Leu Met Leu Glu Asp Leu Ile
                485                     490
```

( 2 ) INFORMATION FOR SEQ ID NO:5:

( i ) SEQUENCE CHARACTERISTICS:
        ( A ) LENGTH: 296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ala Val Gly Ser Lys Ser Phe Ala Thr Ala Ser Lys Leu Phe Asp
1               5                   10                  15

Ala Lys Thr Arg Arg Ser Val Leu Met Leu Tyr Ala Trp Cys Arg His
                20                  25                  30

Cys Asp Asp Val Ile Asp Asp Gln Thr Leu Gly Phe Gln Ala Arg Gln
            35                  40                  45

Pro Ala Leu Gln Thr Pro Glu Gln Arg Leu Met Gln Leu Glu Met Lys
    50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Ala Gln Tyr
                100                 105                 110

Ser Gln Leu Asp Asp Thr Leu Arg Tyr Cys Tyr His Val Ala Gly Val
            115                 120                 125

Val Gly Leu Met Met Ala Gln Ile Met Gly Val Arg Asp Asn Ala Thr
    130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala His Ala Gly Arg Cys Tyr Leu Pro
                165                 170                 175

Ala Ser Trp Leu Glu His Glu Gly Leu Asn Lys Glu Asn Tyr Ala Ala
            180                 185                 190

Pro Glu Asn Arg Gln Ala Leu Ser Arg Ile Ala Arg Arg Leu Val Gln
    195                 200                 205

Glu Ala Glu Pro Tyr Tyr Leu Ser Ala Thr Ala Gly Leu Ala Gly Leu
210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Gln Gln Ala Trp Asp Gln
                245                 250                 255

Arg Gln Ser Thr Thr Thr Pro Glu Lys Leu Thr Leu Leu Leu Ala Ala
            260                 265                 270

Ser Gly Gln Ala Leu Thr Ser Arg Met Arg Ala His Pro Pro Arg Pro
    275                 280                 285

Ala His Leu Trp Gln Arg Pro Leu
290                 295
```

( 2 ) INFORMATION FOR SEQ ID NO:6:

(i) SEQUENCE CHARACTERISTICS:
  (A) LENGTH: 175 amino acids
  (B) TYPE: amino acid
  (D) TOPOLOGY: linear (ii) MOLECULE TYPE: protein (xi) SEQUENCE DESCRIPTION: SEQ ID NO:6:

```
Met Leu Trp Ile Trp Asn Ala Leu Ile Val Phe Val Thr Val Ile Gly
 1           5                  10                  15
Met Glu Val Ile Ala Ala Leu Ala His Lys Tyr Ile Met His Gly Trp
            20                  25                  30
Gly Trp Gly Trp His Leu Ser His His Glu Pro Arg Lys Gly Ala Phe
        35                  40                  45
Glu Val Asn Asp Leu Tyr Ala Val Val Phe Ala Ala Leu Ser Ile Leu
    50                  55                  60
Leu Ile Tyr Leu Gly Ser Thr Gly Met Trp Pro Leu Gln Trp Ile Gly
65                  70                  75                  80
Ala Gly Met Thr Ala Tyr Gly Leu Leu Tyr Phe Met Val His Asp Gly
                85                  90                  95
Leu Val His Gln Arg Trp Pro Phe Arg Tyr Ile Pro Arg Lys Gly Tyr
            100                 105                 110
Leu Lys Arg Leu Tyr Met Ala His Arg Met His His Ala Val Arg Gly
        115                 120                 125
Lys Glu Gly Cys Val Ser Phe Gly Phe Leu Tyr Ala Pro Pro Leu Ser
    130                 135                 140
Lys Leu Gln Ala Thr Leu Arg Glu Arg His Gly Ala Arg Ala Gly Ala
145                 150                 155                 160
Ala Arg Asp Ala Gln Gly Gly Glu Asp Glu Pro Ala Ser Gly Lys
                165                 170                 175
```

(2) INFORMATION FOR SEQ ID NO:7:

(i) SEQUENCE CHARACTERISTICS:
    (A) LENGTH: 909 base pairs
    (B) TYPE: nucleic acid
    (C) STRANDEDNESS: double
    (D) TOPOLOGY: linear (ii) MOLECULE TYPE: other nucleic acid (plasmid DNA)

(xi) SEQUENCE DESCRIPTION: SEQ ID NO:7:

```
ATGACGGTCT GCGCAAAAAA ACACGTTCAT CTCACTCGCG ATGCTGCGGA GCAGTTACTG     60
GCTGATATTG ATCGACGCCT TGATCAGTTA TTGCCCGTGG AGGGAGAACG GGATGTTGTG    120
GGTGCCGCGA TGCGTGAAGG TGCGCTGGCA CCGGGAAAAC GTATTCGCCC CATGTTGCTG    180
TTGCTGACCG CCCGCGATCT GGGTTGCGCT GTCAGCCATG ACGGATTACT GGATTTGGCC    240
TGTGCGGTGG AAATGGTCCA CGCGGCTTCG CTGATCCTTG ACGATATGCC CTGCATGGAC    300
GATGCGAAGC TGCGGCGCGG ACGCCCTACC ATTCATTCTC ATTACGGAGA GCATGTGGCA    360
ATACTGGCGG CGGTTGCCTT GCTGAGTAAA GCCTTTGGCG TAATTGCCGA TGCAGATGGC    420
CTCACGCCGC TGGCAAAAAA TCGGGCGGTT TCTGAACTGT CAAACGCCAT CGGCATGCAA    480
GGATTGGTTC AGGGTCAGTT CAAGGATCTG TCTGAAGGGG ATAAGCCGCG CAGCGCTGAA    540
GCTATTTTGA TGACGAATCA CTTTAAAACC AGCACGCTGT TTGTGCCTC CATGCAGATG    600
GCCTCGATTG TTGCGAATGC CTCCAGCGAA GCGCGTGATT GCCTGCATCG TTTTTCACTT    660
GATCTTGGTC AGGCATTTCA ACTGCTGGAC GATTTGACCG ATGGCATGAC CGACACCGGT    720
AAGGATAGCA ATCAGGACGC CGGTAAATCG ACGCTGGTCA ATCTGTTAGG CCCGAGGGCG    780
```

-continued

| | | | | | |
|---|---|---|---|---|---|
| GTTGAAGAAC | GTCTGAGACA | ACATCTTCAG | CTTGCCAGTG | AGCATCTCTC | TGCGGCCTGC | 840 |
| CAACACGGGC | ACGCCACTCA | ACATTTATT | CAGGCCTGGT | TTGACAAAAA | ACTCGCTGCC | 900 |
| GTCAGTTAA | | | | | 909 |

( 2 ) INFORMATION FOR SEQ ID NO:8:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: other nucleic acid (plasmid DNA)

( x i ) SEQUENCE DESCRIPTION: SEQ ID NO:8:

| | | | | | |
|---|---|---|---|---|---|
| ATGAGCCATT | TCGCGGCGAT | CGCACCGCCT | TTTTACAGCC | ATGTTCGCGC | ATTACAGAAT | 60 |
| CTCGCTCAGG | AACTGGTCGC | GCGCGGTCAT | CGGGTGACCT | TTATTCAGCA | ATACGATATT | 120 |
| AAACACTTGA | TCGATAGCGA | AACCATTGGA | TTTCATTCCG | TCGGGACAGA | CAGCCATCCC | 180 |
| CCCGGCGCGT | TAACGCGCGT | GCTACACCTG | GCGGCTCATC | CTCTGGGGCC | GTCAATGCTG | 240 |
| AAGCTCATCA | ATGAAATGGC | GCGCACCACC | GATATGCTGT | GCCGCGAACT | CCCCCAGGCA | 300 |
| TTTAACGATC | TGGCCGTCGA | TGGCGTCATT | GTTGATCAAA | TGGAACCGGC | AGGCGCGCTC | 360 |
| GTTGCTGAAG | CACTGGGACT | GCCGTTTATC | TCTGTCGCCT | GCGCGCTGCC | TCTCAATCGT | 420 |
| GAACCGGATA | TGCCCCTGGC | GGTTATGCCT | TTCGAATACG | GACCAGCGA | CGCGGCTCGC | 480 |
| GAACGTTATG | CCGCCAGTGA | AAAAATTTAT | GACTGGCTAA | TGCGTCGTCA | TGACCGTGTC | 540 |
| ATTGCCGAAC | ACAGCCACAG | AATGGGCTTA | GCCCCCGGC | AAAAGCTTCA | CCAGTGTTTT | 600 |
| TCGCCACTGG | CGCAAATCAG | CCAGCTTGTT | CCTGAACTGG | ATTTTCCCCG | CAAAGCGTTA | 660 |
| CCGGCTTGTT | TTCATGCCGT | CGGGCCTCTG | CGCGAAACGC | ACGCACCGTC | AACGTCTTCA | 720 |
| TCCCGTTATT | TTACATCCTC | AGAAAAACCC | CGGATTTTCG | CCTCGCTGGG | CACGCTTCAG | 780 |
| GGACACCGTT | ATGGGCTGTT | TAAAACGATA | GTGAAAGCCT | GTGAAGAAAT | TGACGGTCAG | 840 |
| CTCCTGTTAG | CCCACTGTGG | TCGTCTTACG | GACTCTCAGT | GTGAAGAGCT | GGCGCGAAGC | 900 |
| CGTCATACAC | AGGTGGTGGA | TTTTGCCGAT | CAGTCAGCCG | CGCTGTCTCA | GGCGCAGCTG | 960 |
| GCGATCACCC | ACGGCGGCAT | GAATACGGTA | CTGGACGCGA | TTAATTACCG | GACGCCCTT | 1020 |
| TTAGCGCTTC | CGCTGGCCTT | TGATCAGCCC | GGCGTCGCGT | CACGCATCGT | TTATCACGGC | 1080 |
| ATCGGCAAGC | GTGCTTCCCG | CTTTACCACC | AGCCATGCTT | GGCTCGTCA | GATGCGTTCA | 1140 |
| TTGCTGACCA | ACGTCGACTT | TCAGCAGCGC | ATGGCGAAAA | TCCAGACAGC | CCTTCGTTTG | 1200 |
| GCAGGGGGCA | CCATGGCCGC | TGCCGATATC | ATTGAGCAGG | TTATGTGCAC | CGGTCAGCCT | 1260 |
| GTCTTAAGTG | GGAGCGGCTA | TGCAACCGCA | TTATGA | | 1296 |

( 2 ) INFORMATION FOR SEQ ID NO:9:

( i ) SEQUENCE CHARACTERISTICS:
        ( A ) LENGTH: 1149 base pairs
        ( B ) TYPE: nucleic acid
        ( C ) STRANDEDNESS: double
        ( D ) TOPOLOGY: linear ( i i ) MOLECULE TYPE: other nucleic acid (plasmid DNA)

( x i ) SEQUENCE DESCRIPTION: SEQ ID NO:9:

| | | | | | |
|---|---|---|---|---|---|
| ATGCAACCGC | ATTATGATCT | GATTCTCGTG | GGGGCTGGAC | TCGCGAATGG | CCTTATCGCC | 60 |
| CTGCGTCTTC | AGCAGCAGCA | ACCTGATATG | CGTATTTTGC | TTATCGACGC | CGCACCCCAG | 120 |
| GCGGGCGGGA | ATCATACGTG | GTCATTTCAC | CACGATGATT | TGACTGAGAG | CCAACATCGT | 180 |

| | | | | | |
|---|---|---|---|---|---|
| TGGATAGCTC | CGCTGGTGGT | TCATCACTGG | CCCGACTATC | AGGTACGCTT | TCCCACACGC | 240 |
| CGTCGTAAGC | TGAACAGCGG | CTACTTTGT | ATTACTTCTC | AGCGTTTCGC | TGAGGTTTTA | 300 |
| CAGCGACAGT | TTGGCCCGCA | CTTGTGGATG | GATACCGCGG | TCGCAGAGGT | TAATGCGGAA | 360 |
| TCTGTTCGGT | TGAAAAAGGG | TCAGGTTATC | GGTGCCCGCG | CGGTGATTGA | CGGGCGGGGT | 420 |
| TATGCGGCAA | ATTCAGCACT | GAGCGTGGGC | TTCCAGGCGT | TTATTGGCCA | GGAATGGCGA | 480 |
| TTGAGCCACC | CGCATGGTTT | ATCGTCTCCC | ATTATCATGG | ATGCCACGGT | CGATCAGCAA | 540 |
| AATGGTTATC | GCTTCGTGTA | CAGCCTGCCG | CTCTCGCCGA | CCAGATTGTT | AATTGAAGAC | 600 |
| ACGCACTATA | TTGATAATGC | GACATTAGAT | CCTGAATGCG | CGCGGCAAAA | TATTTGCGAC | 660 |
| TATGCCGCGC | AACAGGGTTG | GCAGCTTCAG | ACACTGCTGC | GAGAAGAACA | GGGCGCCTTA | 720 |
| CCCATTACTC | TGTCGGGCAA | TGCCGACGCA | TTCTGGCAGC | AGCGCCCCCT | GGCCTGTAGT | 780 |
| GGATTACGTG | CCGGTCTGTT | CCATCCTACC | ACCGGCTATT | CACTGCCGCT | GGCGGTTGCC | 840 |
| GTGGCCGACC | GCCTGAGTGC | ACTTGATGTC | TTTACGTCGG | CCTCAATTCA | CCATGCCATT | 900 |
| ACGCATTTTG | CCCGCGAGCG | CTGGCAGCAG | CAGGGCTTTT | TCCGCATGCT | GAATCGCATG | 960 |
| CTGTTTTTAG | CCGGACCCGC | CGATTCACGC | TGGCGGGTTA | TGCAGCGTTT | TTATGGTTTA | 1020 |
| CCTGAAGATT | TAATTGCCCG | TTTTTATGCG | GGAAAACTCA | CGCTGACCGA | TCGGCTACGT | 1080 |
| ATTCTGAGCG | GCAAGCCGCC | TGTTCCGGTA | TTAGCAGCAT | TGCAAGCCAT | TATGACGACT | 1140 |
| CATCGTTAA | | | | | | 1149 |

( 2 ) INFORMATION FOR SEQ ID NO:10:

( i ) SEQUENCE CHARACTERISTICS:
          ( A ) LENGTH: 1479 base pairs
          ( B ) TYPE: nucleic acid
          ( C ) STRANDEDNESS: double
          ( D ) TOPOLOGY: linear ( i i ) MOLECULE TYPE: other nucleic acid (plasmid DNA)

( x i ) SEQUENCE DESCRIPTION: SEQ ID NO:10:

| | | | | | |
|---|---|---|---|---|---|
| ATGAAACCAA | CTACGGTAAT | TGGTGCAGGC | TTCGGTGGCC | TGGCACTGGC | AATTCGTCTA | 60 |
| CAAGCTGCGG | GGATCCCCGT | CTTACTGCTT | GAACAACGTG | ATAAACCCGG | CGGTCGGGCT | 120 |
| TATGTCTACG | AGGATCAGGG | GTTTACCTTT | GATGCAGGCC | CGACGGTTAT | CACCGATCCC | 180 |
| AGTGCCATTG | AAGAACTGTT | TGCACTGGCA | GGAAAACAGT | TAAAAGAGTA | TGTCGAACTG | 240 |
| CTGCCGGTTA | CGCCGTTTTA | CCGCCTGTGT | TGGGAGTCAG | GGAAGGTCTT | TAATTACGAT | 300 |
| AACGATCAAA | CCCGGCTCGA | AGCGCAGATT | CAGCAGTTTA | ATCCCCGCGA | TGTCGAAGGT | 360 |
| TATCGTCAGT | TTCTGGACTA | TTCACGCGCG | GTGTTTAAAG | AAGGCTATCT | AAAGCTCGGT | 420 |
| ACTGTCCCTT | TTTTATCGTT | CAGAGACATG | CTTCGCGCCG | CACCTCAACT | GGCGAAACTG | 480 |
| CAGGCATGGA | GAAGCGTTTA | CAGTAAGGTT | GCCAGTTACA | TCGAAGATGA | ACATCTGCGC | 540 |
| CAGGCGTTTT | CTTTCCACTC | GCTGTTGGTG | GGCGGCAATC | CCTTCGCCAC | CTCATCCATT | 600 |
| TATACGTTGA | TACACGCGCT | GGAGCGTGAG | TGGGCGTCT | GGTTTCCGCG | TGGCGGCACC | 660 |
| GGCGCATTAG | TTCAGGGGAT | GATAAAGCTG | TTTCAGGATC | TGGGTGGCGA | AGTCGTGTTA | 720 |
| AACGCCAGAG | TCAGCCATAT | GGAAACGACA | GGAAACAAGA | TTGAAGCCGT | GCATTTAGAG | 780 |
| GACGGTCGCA | GGTTCCTGAC | GCAAGCCGTC | GCGTCAAATG | CAGATGTGGT | TCATACCTAT | 840 |
| CGCGACCTGT | TAAGCCAGCA | CCCTGCCGCG | GTTAAGCAGT | CCAACAAACT | GCAGACTAAG | 900 |
| CGCATGAGTA | ACTCTCTGTT | TGTGCTCTAT | TTTGGTTTGA | ATCACCATCA | TGATCAGCTC | 960 |
| GCGCATCACA | CGGTTTGTTT | CGGCCCGCGT | TACCGCGAGC | TGATTGACGA | AATTTTTAAT | 1020 |
| CATGATGGCC | TCGCAGAGGA | CTTCTCACTT | TATCTGCACG | CGCCCTGTGT | CACGGATTCG | 1080 |

```
TCACTGGCGC CTGAAGGTTG CGGCAGTTAC TATGTGTTGG CGCCGGTGCC GCATTTAGGC    1140
ACCGCGAACC TCGACTGGAC GGTTGAGGGG CCAAAACTAC GCGACCGTAT TTTTGCGTAC    1200
CTTGAGCAGC ATTACATGCC TGGCTTACGG AGTCAGCTGG TCACGCACCG ATGTTTACG     1260
CCGTTTGATT TTCGCGACCA GCTTAATGCC TATCATGGCT CAGCCTTTTC TGTGGAGCCC    1320
GTTCTTACCC AGAGCGCCTG GTTTCGGCCG CATAACCGCG ATAAACCAT TACTAATCTC     1380
TACCTGGTCG CGCAGGCAC GCATCCCGGC GCAGGCATTC CTGGCGTCAT CGGCTCGGCA     1440
AAAGCGACAG CAGGTTTGAT GCTGGAGGAT CTGATTTGA                           1479
```

( 2 ) INFORMATION FOR SEQ ID NO:11:

( i ) SEQUENCE CHARACTERISTICS:
        ( A ) LENGTH: 891 base pairs
        ( B ) TYPE: nucleic acid
        ( C ) STRANDEDNESS: double
        ( D ) TOPOLOGY: linear ( i i ) MOLECULE TYPE: other nucleic acid (plasmid DNA)

( x i ) SEQUENCE DESCRIPTION: SEQ ID NO:11:

```
ATGGCAGTTG GCTCGAAAAG TTTTGCGACA GCCTCAAAGT TATTTGATGC AAAAACCCGG    60
CGCAGCGTAC TGATGCTCTA CGCCTGGTGC CGCCATTGTG ACGATGTTAT TGACGATCAG    120
ACGCTGGGCT TTCAGGCCCG GCAGCCTGCC TTACAAACGC CCGAACAACG TCTGATGCAA    180
CTTGAGATGA AAACGCGCCA GGCCTATGCA GGATCGCAGA TGCACGAACC GGCGTTTGCG    240
GCTTTTCAGG AAGTGGCTAT GGCTCATGAT ATCGCCCCGG CTTACGCGTT TGATCATCTG    300
GAAGGCTTCG CCATGGATGT ACGCGAAGCG CAATACAGCC AACTGGATGA TACGCTGCGC    360
TATTGCTATC ACGTTGCAGG CGTTGTCGGC TTGATGATGG CGCAAATCAT GGGCGTGCGG    420
GATAACGCCA CGCTGGACCG CGCCTGTGAC CTTGGGCTGG CATTTCAGTT GACCAATATT    480
GCTCGCGATA TTGTGGACGA TGCGCATGCG GGCCGCTGTT ATCTGCCGGC AAGCTGGCTG    540
GAGCATGAAG GTCTGAACAA AGAGAATTAT GCGGCACCTG AAAACCGTCA GGCGCTGAGC    600
CGTATCGCCC GTCGTTTGGT GCAGGAAGCA GAACCTTACT ATTTGTCTGC CACAGCCGGC    660
CTGGCAGGGT TGCCCCTGCG TTCCGCCTGG GCAATCGCTA CGGCGAAGCA GGTTTACCGG    720
AAAATAGGTG TCAAAGTTGA ACAGGCCGGT CAGCAAGCCT GGGATCAGCG GCAGTCAACG    780
ACCACGCCCG AAAAATTAAC GCTGCTGCTG GCCGCCTCTG GTCAGGCCCT TACTTCCCGG    840
ATGCGGGCTC ATCCTCCCCG CCCTGCGCAT CTCTGGCAGC GCCCGCTCTA G             891
```

( 2 ) INFORMATION FOR SEQ ID NO:12:

( i ) SEQUENCE CHARACTERISTICS:
        ( A ) LENGTH: 528 base pairs
        ( B ) TYPE: nucleic acid
        ( C ) STRANDEDNESS: double
        ( D ) TOPOLOGY: linear ( i i ) MOLECULE TYPE: other nucleic acid (plasmid DNA)

( x i ) SEQUENCE DESCRIPTION: SEQ ID NO:12:

```
ATGTTGTGGA TTTGGAATGC CCTGATCGTT TTCGTTACCG TGATTGGCAT GGAAGTGATT    60
GCTGCACTGG CACACAAATA CATCATGCAC GGCTGGGGTT GGGGATGGCA TCTTTCACAT    120
CATGAACCGC GTAAAGGTGC GTTTGAAGTT AACGATCTTT ATGCCGTGGT TTTTGCTGCA    180
TTATCGATCC TGCTGATTTA CTGGGCAGT ACAGGAATGT GGCCGCTCCA GTGGATTGGC    240
GCAGGTATGA CGGCGTATGG ATTACTCTAT TTTATGGTGC ACGACGGGCT GGTGCATCAA    300
CGTTGGCCAT TCCGCTATAT TCCACGCAAG GGCTACCTCA AACGGTTGTA TATGGCGCAC    360
```

CGTATGCATC ACGCCGTCAG GGGCAAAGAA GGTTGTGTTT CTTTTGGCTT CCTCTATGCG    420

CCGCCCCTGT CAAAACTTCA GGCGACGCTC CGGGAAAGAC ATGGCGCTAG AGCGGGCGCT    480

GCCAGAGATG CGCAGGGCGG GGAGGATGAG CCCGCATCCG GAAGTAA    528

( 2 ) INFORMATION FOR SEQ ID NO:13:

( i ) SEQUENCE CHARACTERISTICS:
        ( A ) LENGTH: 6918 base pairs
        ( B ) TYPE: nucleic acid
        ( C ) STRANDEDNESS: double
        ( D ) TOPOLOGY: linear ( i i ) MOLECULE TYPE: other nucleic acid (plasmid DNA)

( v i ) ORIGINAL SOURCE:
        ( A ) ORGANISM: Erwinia uredovora
        ( B ) STRAIN: 20D3
        ( G ) CELL TYPE: unicellular organism ( i x ) FEATURE:
        ( A ) NAME/KEY: CDS
            / gene="crt E"
        ( B ) LOCATION: 225 to 1133
        ( C ) IDENTIFICATION METHOD: by experiment
        ( D ) OTHER INFORMATION: codes for geranylgeranyl
            pyrophosphpate synthase
        ( A ) NAME/KEY: CDS
            / gene="crt X"
        ( B ) LOCATION: 1143 to 2438
        ( C ) IDENTIFICATION METHOD: by experiment
        ( D ) OTHER INFORMATION: codes for zeaxanthin glycosilase
        ( A ) NAME/KEY: CDS
            / gene="crt Y"
        ( B ) LOCATION: 2422 to 3570
        ( C ) IDENTIFICATION METHOD: by experiment
        ( D ) OTHER INFORMATION: codes for lycopene cyclase
        ( A ) NAME/KEY: CDS
            / gene="crt I"
        ( B ) LOCATION: 3582 to 5060
        ( C ) IDENTIFICATION METHOD: by experiment
        ( D ) OTHER INFORMATION: codes for phytoene desaturase
        ( A ) NAME/KEY: CDS
            / gene="crt B"
        ( B ) LOCATION: 5096 to 5986
        ( C ) IDENTIFICATION METHOD: by experiment
        ( D ) OTHER INFORMATION: codes for phytoene synthase
        ( A ) NAME/KEY: CDS
            / gene="crt Z"
            / note="on the complementary strand"
        ( B ) LOCATION: 5925 to 6452
        ( C ) IDENTIFICATION METHOD: by experiment
        ( D ) OTHER INFORMATION: codes for β-carotene hydroxylase ( x ) PUBLICATION INFORMATION:
        ( A ) AUTHORS: Misawa, Norihiko
            Nakagawa, Masaya
            Kobayashi, Kazuo
            Yamano, Shigeyuki
            Izawa, Yuko
            Nakamura, Katsumi
            Harashima, Keiji
        ( B ) TITLE: Elucidation of the Erwinia uredovora Carotenoid
            Biosynthesic Path by Functional Analysis of Gene
            Products Expressed in Escheric
        ( C ) JOURNAL: Journal of Bacteriology
        ( D ) VOLUME: 172
        ( E ) ISSUE: 12
        ( F ) PAGES: 6704-6712
        ( G ) DATE: DEC-1990

( x i ) SEQUENCE DESCRIPTION: SEQ ID NO:13:

GGTACCGCAC GGTCTGCCAA TCCGACGGAG GTTTATGAAT TTTCCACCTT TTCCACAAGC    60

TCAACTAGTA TTAACGATGT GGATTTAGCA AAAAAAACCT GTAACCCTAA ATGTAAAATA    120

ACGGGTAAGC CTGCCAACCA TGTTATGGCA GATTAAGCGT CTTTTTGAAG GGCACCGCAT    180

-continued

| | | | | | |
|---|---|---|---|---|---|
| CTTTCGCGTT | GCCGTAAATG | TATCCGTTTA | TAAGGACAGC | CCGAATGACG | GTCTGCGCAA | 240 |
| AAAAACACGT | TCATCTCACT | CGCGATGCTG | CGGAGCAGTT | ACTGGCTGAT | ATTGATCGAC | 300 |
| GCCTTGATCA | GTTATTGCCC | GTGGAGGGAG | AACGGGATGT | TGTGGGTGCC | GCGATGCGTG | 360 |
| AAGGTGCGCT | GGCACCGGGA | AAACGTATTC | GCCCCATGTT | GCTGTTGCTG | ACCGCCCGCG | 420 |
| ATCTGGGTTG | CGCTGTCAGC | CATGACGGAT | TACTGGATTT | GGCCTGTGCG | GTGGAAATGG | 480 |
| TCCACGCGGC | TTCGCTGATC | CTTGACGATA | TGCCCTGCAT | GGACGATGCG | AAGCTGCGGC | 540 |
| GCGGACGCCC | TACCATTCAT | TCTCATTACG | GAGAGCATGT | GGCAATACTG | GCGGCGGTTG | 600 |
| CCTTGCTGAG | TAAAGCCTTT | GGCGTAATTG | CCGATGCAGA | TGGCCTCACG | CCGCTGGCAA | 660 |
| AAAATCGGGC | GGTTTCTGAA | CTGTCAAACG | CCATCGGCAT | GCAAGGATTG | GTTCAGGGTC | 720 |
| AGTTCAAGGA | TCTGTCTGAA | GGGGATAAGC | CGCGCAGCGC | TGAAGCTATT | TTGATGACGA | 780 |
| ATCACTTTAA | AACCAGCACG | CTGTTTTGTG | CCTCCATGCA | GATGGCCTCG | ATTGTTGCGA | 840 |
| ATGCCTCCAG | CGAAGCGCGT | GATTGCCTGC | ATCGTTTTC | ACTTGATCTT | GGTCAGGCAT | 900 |
| TTCAACTGCT | GGACGATTTG | ACCGATGGCA | TGACCGACAC | CGGTAAGGAT | AGCAATCAGG | 960 |
| ACGCCGGTAA | ATCGACGCTG | GTCAATCTGT | TAGGCCCGAG | GGCGGTTGAA | GAACGTCTGA | 1020 |
| GACAACATCT | TCAGCTTGCC | AGTGAGCATC | TCTCTGCGGC | CTGCCAACAC | GGGCACGCCA | 1080 |
| CTCAACATTT | TATTCAGGCC | TGGTTTGACA | AAAAACTCGC | TGCCGTCAGT | TAAGGATGCT | 1140 |
| GCATGAGCCA | TTTCGCGGCG | ATCGCACCGC | CTTTTTACAG | CCATGTTCGC | GCATTACAGA | 1200 |
| ATCTCGCTCA | GGAACTGGTC | GCGCGCGGTC | ATCGGGTGAC | CTTTATTCAG | CAATACGATA | 1260 |
| TTAAACACTT | GATCGATAGC | GAAACCATTG | GATTTCATTC | CGTCGGGACA | GACAGCCATC | 1320 |
| CCCCCGGCGC | GTTAACGCGC | GTGCTACACC | TGGCGGCTCA | TCCTCTGGGG | CCGTCAATGC | 1380 |
| TGAAGCTCAT | CAATGAAATG | GCGCGCACCA | CCGATATGCT | GTGCCGCGAA | CTCCCCCAGG | 1440 |
| CATTTAACGA | TCTGGCCGTC | GATGGCGTCA | TTGTTGATCA | AATGGAACCG | GCAGGCGCGC | 1500 |
| TCGTTGCTGA | AGCACTGGGA | CTGCCGTTTA | TCTCTGTCGC | CTGCGCGCTG | CCTCTCAATC | 1560 |
| GTGAACCGGA | TATGCCCCTG | GCGGTTATGC | CTTTCGAATA | CGGGACCAGC | GACGCGGCTC | 1620 |
| GCGAACGTTA | TGCCGCCAGT | GAAAAAATTT | ATGACTGGCT | AATGCGTCGT | CATGACCGTG | 1680 |
| TCATTGCCGA | ACACAGCCAC | AGAATGGGCT | TAGCCCCCCG | GCAAAAGCTT | CACCAGTGTT | 1740 |
| TTTCGCCACT | GGCGCAAATC | AGCCAGCTTG | TTCCTGAACT | GGATTTTCCC | CGCAAAGCGT | 1800 |
| TACCGGCTTG | TTTTCATGCC | GTCGGGCCTC | TGCGCGAAAC | GCACGCACCG | TCAACGTCTT | 1860 |
| CATCCCGTTA | TTTTACATCC | TCAGAAAAAC | CCCGGATTTT | CGCCTCGCTG | GGCACGCTTC | 1920 |
| AGGGACACCG | TTATGGGCTG | TTTAAAACGA | TAGTGAAAGC | CTGTGAAGAA | ATTGACGGTC | 1980 |
| AGCTCCTGTT | AGCCCACTGT | GGTCGTCTTA | CGGACTCTCA | GTGTGAAGAG | CTGGCGCGAA | 2040 |
| GCCGTCATAC | ACAGGTGGTG | GATTTGCCG | ATCAGTCAGC | CGCGCTGTCT | CAGGCGCAGC | 2100 |
| TGGCGATCAC | CCACGGCGGC | ATGAATACGG | TACTGGACGC | GATTAATTAC | CGGACGCCCC | 2160 |
| TTTTAGCGCT | TCCGCTGGCC | TTTGATCAGC | CGGCGTCGC | GTCACGCATC | GTTTATCACG | 2220 |
| GCATCGGCAA | GCGTGCTTCC | CGCTTTACCA | CCAGCCATGC | TTTGGCTCGT | CAGATGCGTT | 2280 |
| CATTGCTGAC | CAACGTCGAC | TTTCAGCAGC | GCATGGCGAA | AATCCAGACA | GCCCTTCGTT | 2340 |
| TGGCAGGGGG | CACCATGGCC | GCTGCCGATA | TCATTGAGCA | GGTTATGTGC | ACCGGTCAGC | 2400 |
| CTGTCTTAAG | TGGGAGCGGC | TATGCAACCG | CATTATGATC | TGATTCTCGT | GGGGGCTGGA | 2460 |
| CTCGCGAATG | GCCTTATCGC | CCTGCGTCTT | CAGCAGCAGC | AACCTGATAT | GCGTATTTTG | 2520 |
| CTTATCGACG | CCGCACCCCA | GGCGGGCGGG | AATCATACGT | GGTCATTTCA | CCACGATGAT | 2580 |
| TTGACTGAGA | GCCAACATCG | TTGGATAGCT | CCGCTGGTGG | TTCATCACTG | GCCCGACTAT | 2640 |

-continued

| | | | | | |
|---|---|---|---|---|---|
| CAGGTACGCT | TTCCCACACG | CCGTCGTAAG | CTAACAGCG | GCTACTTTTG | TATTACTTCT | 2700 |
| CAGCGTTTCG | CTGAGGTTTT | ACAGCGACAG | TTTGGCCCGC | ACTTGTGGAT | GGATACCGCG | 2760 |
| GTCGCAGAGG | TTAATGCGGA | ATCTGTTCGG | TTGAAAAGG | GTCAGGTTAT | CGGTGCCCGC | 2820 |
| GCGGTGATTG | ACGGGCGGGG | TTATGCGGCA | AATTCAGCAC | TGAGCGTGGG | CTTCCAGGCG | 2880 |
| TTTATTGGCC | AGGAATGGCG | ATTGAGCCAC | CCGCATGGTT | TATCGTCTCC | CATTATCATG | 2940 |
| GATGCCACGG | TCGATCAGCA | AAATGGTTAT | CGCTTCGTGT | ACAGCCTGCC | GCTCTCGCCG | 3000 |
| ACCAGATTGT | TAATTGAAGA | CACGCACTAT | ATTGATAATG | CGACATTAGA | TCCTGAATGC | 3060 |
| GCGCGGCAAA | ATATTTGCGA | CTATGCCGCG | CAACAGGGTT | GGCAGCTTCA | GACACTGCTG | 3120 |
| CGAGAAGAAC | AGGGCGCCTT | ACCCATTACT | CTGTCGGGCA | ATGCCGACGC | ATTCTGGCAG | 3180 |
| CAGCGCCCCC | TGGCCTGTAG | TGGATTACGT | GCCGGTCTGT | TCCATCCTAC | CACCGGCTAT | 3240 |
| TCACTGCCGC | TGGCGGTTGC | CGTGGCCGAC | CGCCTGAGTG | CACTTGATGT | CTTTACGTCG | 3300 |
| GCCTCAATTC | ACCATGCCAT | TACGCATTTT | GCCCGCGAGC | GCTGGCAGCA | GCAGGGCTTT | 3360 |
| TTCCGCATGC | TGAATCGCAT | GCTGTTTTTA | GCCGGACCCG | CCGATTCACG | CTGGCGGGTT | 3420 |
| ATGCAGCGTT | TTTATGGTTT | ACCTGAAGAT | TTAATTGCCC | GTTTTATGC | GGGAAAACTC | 3480 |
| ACGCTGACCG | ATCGGCTACG | TATTCTGAGC | GGCAAGCCGC | CTGTTCCGGT | ATTAGCAGCA | 3540 |
| TTGCAAGCCA | TTATGACGAC | TCATCGTTAA | AGAGCGACTA | CATGAAACCA | ACTACGGTAA | 3600 |
| TTGGTGCAGG | CTTCGGTGGC | CTGGCACTGG | CAATTCGTCT | ACAAGCTGCG | GGATCCCCG | 3660 |
| TCTTACTGCT | TGAACAACGT | GATAAACCCG | GCGGTCGGGC | TTATGTCTAC | GAGGATCAGG | 3720 |
| GGTTTACCTT | TGATGCAGGC | CCGACGGTTA | TCACCGATCC | CAGTGCCATT | GAAGAACTGT | 3780 |
| TTGCACTGGC | AGGAAAACAG | TTAAAAGAGT | ATGTCGAACT | GCTGCCGGTT | ACGCCGTTTT | 3840 |
| ACCGCCTGTG | TTGGGAGTCA | GGGAAGGTCT | TTAATTACGA | TAACGATCAA | ACCCGGCTCG | 3900 |
| AAGCGCAGAT | TCAGCAGTTT | AATCCCCGCG | ATGTCGAAGG | TTATCGTCAG | TTTCTGGACT | 3960 |
| ATTCACGCGC | GGTGTTTAAA | GAAGGCTATC | TAAAGCTCGG | TACTGTCCCT | TTTTTATCGT | 4020 |
| TCAGAGACAT | GCTTCGCGCC | GCACCTCAAC | TGGCGAAACT | GCAGGCATGG | AGAAGCGTTT | 4080 |
| ACAGTAAGGT | TGCCAGTTAC | ATCGAAGATG | AACATCTGCG | CCAGGCGTTT | TCTTTCCACT | 4140 |
| CGCTGTTGGT | GGGCGGCAAT | CCCTTCGCCA | CCTCATCCAT | TTATACGTTG | ATACACGCGC | 4200 |
| TGGAGCGTGA | GTGGGGCGTC | TGGTTTCCGC | GTGGCGGCAC | CGGCGCATTA | GTTCAGGGGA | 4260 |
| TGATAAAGCT | GTTTCAGGAT | CTGGGTGGCG | AAGTCGTGTT | AAACGCCAGA | GTCAGCCATA | 4320 |
| TGGAAACGAC | AGGAAACAAG | ATTGAAGCCG | TGCATTTAGA | GGACGGTCGC | AGGTTCCTGA | 4380 |
| CGCAAGCCGT | CGCGTCAAAT | GCAGATGTGG | TTCATACCTA | TCGCGACCTG | TTAAGCCAGC | 4440 |
| ACCCTGCCGC | GGTTAAGCAG | TCCAACAAAC | TGCAGACTAA | GCGCATGAGT | AACTCTCTGT | 4500 |
| TTGTGCTCTA | TTTTGGTTTG | AATCACCATC | ATGATCAGCT | CGCGCATCAC | ACGGTTTGTT | 4560 |
| TCGGCCCGCG | TTACCGCGAG | CTGATTGACG | AAATTTTTAA | TCATGATGGC | CTCGCAGAGG | 4620 |
| ACTTCTCACT | TATCTGCAC | GCGCCCTGTG | TCACGGATTC | GTCACTGGCG | CCTGAAGGTT | 4680 |
| GCGGCAGTTA | CTATGTGTTG | GCGCCGGTGC | CGCATTTAGG | CACCGCGAAC | CTCGACTGGA | 4740 |
| CGGTTGAGGG | GCCAAAACTA | CGCGACCGTA | TTTTTGCGTA | CCTTGAGCAG | CATTACATGC | 4800 |
| CTGGCTTACG | GAGTCAGCTG | GTCACGCACC | GGATGTTTAC | GCCGTTTGAT | TTTCGCGACC | 4860 |
| AGCTTAATGC | CTATCATGGC | TCAGCCTTTT | CTGTGGAGCC | CGTTCTTACC | CAGAGCGCCT | 4920 |
| GGTTTCGGCC | GCATAACCGC | GATAAAACCA | TTACTAATCT | CTACCTGGTC | GGCGCAGGCA | 4980 |
| CGCATCCCGG | CGCAGGCATT | CCTGGCGTCA | TCGGCTCGGC | AAAAGCGACA | GCAGGTTTGA | 5040 |
| TGCTGGAGGA | TCTGATTTGA | ATAATCCGTC | GTTACTCAAT | CATGCGGTCG | AAACGATGGC | 5100 |

| AGTTGGCTCG | AAAAGTTTTG | CGACAGCCTC | AAAGTTATTT | GATGCAAAAA | CCCGGCGCAG | 5160 |
| AGTTGGCTCG | AAAAGTTTTG | CGACAGCCTC | AAAGTTATTT | GATGCAAAAA | CCCGGCGCAG | 5160 |
| CGTACTGATG | CTCTACGCCT | GGTGCCGCCA | TTGTGACGAT | GTTATTGACG | ATCAGACGCT | 5220 |
| GGGCTTTCAG | GCCCGGCAGC | CTGCCTTACA | AACGCCCGAA | CAACGTCTGA | TGCAACTTGA | 5280 |
| GATGAAAACG | CGCCAGGCCT | ATGCAGGATC | GCAGATGCAC | GAACCGGCGT | TGCGGCTTT | 5340 |
| TCAGGAAGTG | GCTATGGCTC | ATGATATCGC | CCCGGCTTAC | GCGTTTGATC | ATCTGGAAGG | 5400 |
| CTTCGCCATG | GATGTACGCG | AAGCGCAATA | CAGCCAACTG | GATGATACGC | TGCGCTATTG | 5460 |
| CTATCACGTT | GCAGGCGTTG | TCGGCTTGAT | GATGGCGCAA | ATCATGGGCG | TGCGGGATAA | 5520 |
| CGCCACGCTG | GACCGCGCCT | GTGACCTTGG | GCTGGCATTT | CAGTTGACCA | ATATTGCTCG | 5580 |
| CGATATTGTG | GACGATGCGC | ATGCGGGCCG | CTGTTATCTG | CCGGCAAGCT | GGCTGGAGCA | 5640 |
| TGAAGGTCTG | AACAAAGAGA | ATTATGCGGC | ACCTGAAAAC | CGTCAGGCGC | TGAGCCGTAT | 5700 |
| CGCCCGTCGT | TTGGTGCAGG | AAGCAGAACC | TTACTATTTG | TCTGCCACAG | CCGGCCTGGC | 5760 |
| AGGGTTGCCC | CTGCGTTCCG | CCTGGGCAAT | CGCTACGGCG | AAGCAGGTTT | ACCGGAAAAT | 5820 |
| AGGTGTCAAA | GTTGAACAGG | CCGGTCAGCA | AGCCTGGGAT | CAGCGGCAGT | CAACGACCAC | 5880 |
| GCCCGAAAAA | TTAACGCTGC | TGCTGGCCGC | CTCTGGTCAG | GCCCTTACTT | CCCGGATGCG | 5940 |
| GGCTCATCCT | CCCCGCCCTG | CGCATCTCTG | GCAGCGCCCG | CTCTAGCGCC | ATGTCTTTCC | 6000 |
| CGGAGCGTCG | CCTGAAGTTT | TGACAGGGGC | GGCGCATAGA | GGAAGCCAAA | AGAAACACAA | 6060 |
| CCTTCTTTGC | CCCTGACGGC | GTGATGCATA | CGGTGCGCCA | TATACAACCG | TTTGAGGTAG | 6120 |
| CCCTTGCGTG | GAATATAGCG | GAATGGCCAA | CGTTGATGCA | CCAGCCCGTC | GTGCACCATA | 6180 |
| AAATAGAGTA | ATCCATACGC | CGTCATACCT | GCGCCAATCC | ACTGGAGCGG | CCACATTCCT | 6240 |
| GTACTGCCCA | GATAAATCAG | CAGGATCGAT | AATGCAGCAA | AAACCACGGC | ATAAAGATCG | 6300 |
| TTAACTTCAA | ACGCACCTTT | ACGCGGTTCA | TGATGTGAAA | GATGCCATCC | CCAACCCCAG | 6360 |
| CCGTGCATGA | TGTATTTGTG | TGCCAGTGCA | GCAATCACTT | CCATGCCAAT | CACGGTAACG | 6420 |
| AAAACGATCA | GGGCATTCCA | AATCCACAAC | ATAATTTCTC | CGGTAGAGAC | GTCTGGCAGC | 6480 |
| AGGCTTAAGG | ATTCAATTTT | AACAGAGATT | AGCCGATCTG | GCGGCGGGAA | GGGAAAAAGG | 6540 |
| CGCGCCAGAA | AGGCGCGCCA | GGGATCAGAA | GTCGGCTTTC | AGAACCACAC | GGTAGTTGGC | 6600 |
| TTTACCTGCA | CGAACATGGT | CCAGTGCATC | GTTGATTTTC | GACATCGGGA | AGTACTCCAC | 6660 |
| TGTCGGCGCA | ATATCTGTAC | GGCCAGCCAG | CTTCAGCAGT | GAACGCAGCT | GCGCAGGTGA | 6720 |
| ACCGGTTGAA | GAACCCGTCA | CGGCGCGGTC | GCCTAAAATC | AGGCTGAAAG | CCGGGCACGT | 6780 |
| CAAACGGCTT | CAGTACGGCA | CCCACGGTAT | GGAACTTACC | GCGAGGCGCC | AGGGCCGCAA | 6840 |
| AGTAGGGTTG | CCAGTCGAGA | TCGACGGCGA | CCGTGCTGAT | AATCAGGTCA | AACTGGCCCG | 6900 |
| CCAGGCTTTT | TAAAGCTT | | | | | 6918 |

(2) INFORMATION FOR SEQ ID NO:14:

(i) SEQUENCE CHARACTERISTICS:
        (A) LENGTH: 10 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:14:

GCAGTTGGCT    10

(2) INFORMATION FOR SEQ ID NO:15:

(i) SEQUENCE CHARACTERISTICS:
        (A) LENGTH: 16 bases (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:15:

CGAGCCAACT GCCATG            16

(2) INFORMATION FOR SEQ ID NO:16:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:16:

ACGACTCATC TAGAAGGAGC GACTAC    26

(2) INFORMATION FOR SEQ ID NO:17:

(i) SEQUENCE CHARACTERISTICS:
        (A) LENGTH: 60 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:17:

GATCCCCGGG AGCGGCTATG CAACCGCATT ATGATCTGAT TCTCGTGGGG GCTGGACTCG    60

(2) INFORMATION FOR SEQ ID NO:18:

(i) SEQUENCE CHARACTERISTICS:
        (A) LENGTH: 56 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:18:

CGAGTCCAGC CCCCACGAGA ATCAGATCAT AATGCGGTTG CATAGCCGCT CCCGGG    56

DNA SEQUENCES USEFUL FOR THE SYNTHESIS OF CAROTENOIDS

RELATED APPLICATION DATE

This application is a continuation-in-part application of application Ser. No. 07/519,011, filed on Apr. 19, 1990, now abandoned.

FIELD OF THE INVENTION

The present invention relates to DNA sequences which are useful for the synthesis of carotenoids such as lycopene, β-carotene, zeaxanthin or zeaxanthin-diglucoside.

The present invention also relates to processes for producing such carotenoid compounds.

BACKGROUND OF THE INVENTION

Carotenoids are widely distributed over green plants. They are yellow-orange-red lipids which are also present in some mold, yeast and so forth, and have recently received increased attention as natural coloring materials for foods. Among these carotenoids, β-carotene is a typical one, which is used as a coloring materials and as a precursor of vitamin A in mammals as well. It is also expected to be useful for preventing cancer [see, for example, SHOKUHIN TO KAIHATSU (Foods and Development), 24, 61–65 (1989)]. Since carotenoids such as β-carotene are widely distributed over green plants, plant tissue culture has been examined as a means to produce carotenoids in a large amount without the influence of natural environment [see, for example, Plant Cell Physiol., 12, 525–531 (1971)]. Examination has also been made to search for a microorganism such as mold, yeast or green algae with a high carotenoid producing activity and to produce carotenoids in a large amount using such microorganism (see, for example, The Abstract of Reports in the Annual Meeting of NIPPON HAKKO KOGAKU-KAI of 1988, page 139). However, neither of these is successful at present in producing β-carotene at a good productivity which exceeds synthetic methods in commercial production. It would be very useful to obtain a gene group which participates in the biosynthesis of carotenoids, because it will be possible to produce carotenoids in a larger amount by introducing and expressing appropriate gene(s) among such group in an appropriate host such as a plant tissue cultured cell, a mold, a yeast or the like which originally produces carotenoids. This will lead to a β-carotene production superior to synthetic methods, or to the production of useful carotenoids other than β-carotene in a large amount.

Furthermore, the gene group participating in the biosynthesis of carotenoids would make it possible to synthesize carotenoids in a cell or an organ which originally has no carotenoid producing ability, which will add new values to the organism. For example, several reports have recently been made with reference to creating flower colors not found in nature by the genetic manipulation of flowering plants [see, for example, Nature, 330, 677–678 (1987)]. Flower colors are given by pigments such as anthocyanin and carotenoids. Anthocyanin is responsible for flower colors of red-violet-blue, and carotenoids are responsible for flower colors of yellow-orange-red. Genes encoding enzymes involved in anthocyanin synthesis have been elucidated, which were used for creating a new flower color in the aforementioned reports. On the other hand, there are many flowering plants having no bright yellow flower due to lack of carotenoid synthesis in petals (e.g. petunia, saintpaulia (African violet), cyclamen, Primula malacoides, etc.). Expression of appropriate reconstructed gene(s) for carotenoid biosynthesis in petals would give yellow flowers to these flowering plants.

However, enzymes for synthesizing carotenoids or genes coding for them are scarcely elucidated at present. The nucleotide sequence of the gene group participating in the biosynthesis of a kind of carotenoids has been elucidated lately in a photosynthetic bacterium Rhodobacter capsulatus [Mol. Gen. Genet., 216, 254–268 (1989)]. This bacterium, however, synthesizes an acyclic xanthophyll spheroidene via neurosporene without cyclization and thus cannot synthesize general carotenoids such as lycopene, β-carotene and zeaxanthin.

There are prior arts with reference to yellow pigments or carotenoids of Erwinia species disclosed in J. Bacteriol., 168, 607–612 (1986), J. Bacteriol., 170, 4675–4680 (1988) and J. Gen. Microbiol., 130, 1623–1631 (1984). The first one of these references discloses the cloning of a gene cluster coding for yellow pigment synthesis from Erwinia herbicola Eho 10 ATCC 39368 as a 12.4 kilobase pairs (kb) fragment. There is no information on the nucleotide sequence of the 12.4 kb fragment. The second literature discloses a yellow pigment synthesized by the cloned gene cluster, which is indicated to be a carotenoid by the analysis of its UV-visible spectrum. The last literature indicates that the genes participating in the production of yellow pigments in Erwinia uredovora 20D3 ATCC 19321 are present on a 260 kb large plasmid from the observation that the yellow pigments are not produced after curing the large plasmid, and further discloses that the pigments are carotenoids flora the analysis of their UV-visible spectrum.

However, the chemical structures of the carotenoids and their precursors produced by the Erwinia species, enzymes participating in their synthesis or the nucleotide sequences of the genes encoding these enzymes have been unknown. Very recently, an international patent application was published (WO 91/13078, published on Sep. 5, 1991) which discloses the isolation and nucleotide sequences of the carotenoid synthesis genes of Erwinia herbicola Eho 10 and their expression in several organisms.

SUMMARY OF THE INVENTION

The object of the present invention is to provide DNA sequences which are useful for the synthesis of carotenoids such as lycopene, β-carotene, zeaxanthin or zeaxanthin-diglucoside; DNA sequences encoding casotenoid biosynthesis enzymes.

In other words, the DNA sequences useful for the synthesis of carotenoids according to the present invention are the DNA sequences 1–6 described in the following (1)–(6).

(1) DNA sequence 1: a DNA sequence encoding a polypeptide which has an enzymatic activity for converting farnesyl pyrophosphate into geranylgeranyl pyrophosphate and whose amino acid sequence corresponds substantially to the amino acid sequence of SEQ ID NO:1;

(2) DNA sequence 2: a DNA sequence encoding a polypeptide which has an enzymatic activity for converting zeaxanthin into zeaxanthin-diglucoside and whose. amino acid sequence corresponds substantially to the amino acid sequence of SEQ ID NO:2;

(3) DNA sequence 3: a DNA sequence encoding a polypeptide which has an enzymatic activity for converting lycopene into β-carotene and whose amino acid sequence corresponds substantially to the amino acid sequence of SEQ ID NO:3;

(4) DNA sequence 4: a DNA sequence encoding a polypeptide which has an enzymatic activity for converting phytoene into lycopene and whose amino acid sequence corresponds substantially to the amino acid sequence of SEQ ID NO:4;

(5) DNA sequence 5: a DNA sequence encoding a polypeptide which has an enzymatic activity for converting geranylgeranyl pyrophosphate into phytoene and whose amino acid sequence corresponds substantially to the amino acid sequence of SEQ ID NO:5; and (6) DNA sequence 6: a DNA sequence encoding a polypeptide which has an enzymatic activity for converting β-carotene into zeaxanthin and whose amino acid sequence corresponds substantially to the amino acid sequence of SEQ ID NO:6.

Another object of the present invention is to provide processes for producing carotenoid compounds.

More specifically, the present invention also provides a process for producing a carotenoid or a precursor compound which is selected from the group consisting of geranylgeranyl pyrophosphate, phytoene, lycopene, β-carotene, zeaxanthin and zeaxanthin-diglucoside, which comprises transforming a host with at least one of the DNA sequences 1-6 described above and culturing the transformant.

The successful acquirement of the gene group useful for the synthesis of carotenoids such as lycopene, β-carotene, zeaxanthin, zeaxanthin-diglucoside or the like (gene group encoding the biosynthetic enzymes of carotenoids) according to the present invention has made it possible to produce useful carotenoids in large amounts, for example, by employing an appropriate plant tissue cultured cell, a microorganism or the like transformed with a plasmid capable of expressing the gene(s) to a high level. The present invention has also made it possible to synthesize carotenoids in cells or organs which produce no carotenoid by creating a plasmid in which the gene(s) can be expressed in the target cell or organ and transforming a suitable host with this plasmid.

DETAILED DESCRIPTION OF THE INVENTION

The DNA sequences according to the present invention are the aforementioned DNA sequences 1-6, that is, genes encoding the polypeptides of respective enzymes which participate in the biosynthesis reaction of carotenoids, particular, for example, such polypeptides in *Erwinia uredovora* 20D3 ATCC 19321.

A variety of gene groups containing a combination of the DNA sequences 1-6 can be expressed in a microorganism, a plant or the like to afford them the biosynthesis ability of carotenoids such as lycopene, β-carotene, zeaxanthin, zeaxanthin-diglucoside or the like. The DNA sequences may be present on a single DNA strand (genomic DNA or a plasmid), or on multiple separate DNA strands genomic DNA and/or plasmids) individually or in groups.

The aforementioned gene groups encode a plurality of enzymes participating in the production of carotenoids. It can be incorporated into a proper vector and then introduced into a suitable host to create a transformant. Culturing the transformant will result in the production of the plurality of enzymes participating in carotenoid formation, which will synthesize the carotenoids in the transformant.

The DNA sequence of SEQ ID NO:13, which is an example according to the present invention, is acquired from *Erwinia uredovora* 20D3 ATCC 19321 and shows, as illustrated in the experimental example below, no homology by DNA-DNA hybridization with the DNA strand containing the gene group for synthesizing the yellow pigments of *Erwinia herbicola* Eho 10 ATCC 39368 (see Background of the Invention described above).

The DNA sequences of the present invention are the DNA sequences 1-6 which contain nucleotide sequences encoding a polypeptide whose amino acid sequence corresponds substantially to one of the amino acid sequences of SEQ ID NO:1 to 6. In the present invention, the "DNA sequence" is defined by the amino acid sequence of the polypeptide encoded by the DNA sequence so that each "DNA sequence" has a definite length according to the length of the polypeptide. Although the "DNA sequence" contains a gene encoding an enzyme and is useful for biotechnological production of the enzyme, such biotechnological production cannot be performed by the "DNA sequence" of the definite length alone but in a state where other DNA sequences with a proper length are linked to the 5'-upstream and/or the 3'-downstream of the "DNA sequence". The term "DNA sequence" in the present invention therefore includes, in addition to those having the definite length, a linear DNA strand or a circular DNA strand containing this "DNA sequence" as its part.

One of the typical forms of the DNA sequences of the present invention is a plasmid which comprises the DNA sequences as its part, which may be present in a host such as *E. coli*. A preferable plasmid according to the present invention is a replicable plasmid that is maintained stably in the host carrying the DNA sequences of the present invention, as a passenger or a foreign gene, linked to a promoter(s) (containing the ribosome-binding site in the case of a prokaryotic host). As the plasmid vector and the promoter, an appropriate combination of those which are well-known can be used.

Polypeptides encoded by the DNA sequences

The polypeptides encoded by the DNA sequences of the present invention have an amino acid sequence which corresponds substantially to one of the amino acid sequences of SEQ ID NO:1 to 6. Here, in the six polypeptides of SEQ ID NO:1 to 6 (i.e. six enzymes participating in the formation of carotenoids), some of the amino acids can be deleted or substituted or some amino acids can be added or inserted, so long as each polypeptide has the aforementioned enzymatic activity in terms of substrate-product conversion. This is represented by the expression "whose amino acid sequence corresponds substantially to ..." in the claims. For example, polypeptides with a deletion of the first amino acid (Met) from the polypeptides of SEQ ID NO:1 to 6 are included in such deleted polypeptides.

The amino acid sequences of SEQ ID NO:1 to 6 have not been known before.

Nucleotide sequences of the DNA sequences

The DNA sequences encoding these enzymes are those having one of the nucleotide sequences of SEQ ID NO: 7 to 12 and degenerative isomers thereof, or those having the nucleotide sequences corresponding to an aforementioned alteration of the amino acid sequence of these enzymes and degenerative isomers thereof. The term "degenerative isomer" means a DNA sequence which is different only in degenerative codons and codes for the same polypeptide. The 5'-upstream and/or the 3'-downstream of the DNA sequences of the present invention may further have a DNA sequence with a certain length as non-coding regions.

Gene groups used for the synthesis of carotenoids

The gene groups used for the synthesis of carotenoid, whose typical examples are described in the following (1)-(4), comprise a plurality of the aforementioned DNA sequences 1-6. Each gene group encodes a plurality of enzymes which participate in the production of carotenoids from their substrates.

(1) A gene group used for the synthesis of lycopene

One example of a gene group used for the synthesis of lycopene, a red carotenoid, comprises the aforementioned DNA sequences 1, 4 and 5. The DNA sequences may be present on one DNA strand, or on separate multiple DNA strands individually or in groups.

In the case that a plurality of DNA sequences are present on one DNA strand, the arrangement order and direction of the DNA sequences may be optional provided that the genetic information is expressed, i.e. the genes are in a state capable of being transcribed and translated appropriately in the host.

The biosynthetic pathway of lycopene in $E.\ coli$ is explained as follows: geranylgeranyl pyrophosphate which is a substrate originally present in $E.\ coli$ is converted into phytoene by the enzyme encoded by the DNA sequence 5 and the phytoene is further convened into lycopene by the enzyme encoded by the DNA sequence 4. The enzyme encoded by the DNA sequence I converts farnesyl pyrophosphate into geranylgeranyl pyrophosphate and thus is necessary to increase the production of lycopene (see FIG. 2).

Lycopene is a red carotenoid. It is present in a large amount in the fruits of watermelon or tomato and is highly safe to eat. In this connection, the lycopene synthesized by the DNA sequences of the present invention in the experimental example described below had the same stereochemistry as the lycopene present in these plants.

The gene group is typically on a plasmid with a stop codon for each gene, which plasmid may or may not be present in a host such as $E.\ coil$. A preferable plasmid according to the present invention is a replicable plasmid maintained stably in the host carrying the gene group, as a passenger or a foreign gene, linked to a promoter(s) (containing ribosome-binding sites in the case of a procaryote). In procaryotes such as $E.\ coil$ or Zytnomonas species, a single promoter can be used to express all the DNA sequences, or alternatively each DNA sequence may have its own promoter. In the case of eucaryotes such as a yeast or a plant, each DNA sequence preferably has its own promoter.

(2) A gene group used for the synthesis of β-carotene

One example of a gene group used for the synthesis of β-carotene, a yellow-orange carotenoid, comprises the aforementioned DNA sequences 1, 3, 4 and 5. In other words, the gene group used for the synthesis of β-carotene is formed by adding the DNA sequence 3 to the gene group used for the synthesis of lycopene comprising the DNA sequences 1, 4, and 5. The DNA sequences may be present on one DNA strand, or on separate multiple DNA strands individually or in groups.

In the case that a plurality of DNA sequences are present on one DNA strand, the arrangement order and direction of the aforementioned DNA sequences may be optional provided that the genetic information is expressed, i.e. the genes are in a state capable of being transcribed and translated appropriately in the host.

The biosynthetic pathway of β-carotene in $E.\ coli$ is explained as follows: geranylgeranyl pyrophosphate which is a substrate originally present in $E.\ coli$ is converted into phytoene by the enzyme encoded by the DNA sequence 5 the phytoene is further converted into lycopene by the enzyme encoded by the DNA sequence 4, and the lycopene is further convened into β-carotene by the enzyme encoded by the DNA sequence 3. The enzyme encoded by the DNA sequence 1 converts farnesyl pyrophosphate into geranylgeranyl pyrophosphate and thus is necessary to increase the production of lycopene (see FIG. 2).

β-carotene is a typical carotene with a color spectrum ranging from yellow to orange, and it is the orange pigment present in a large amount in the roots of carrot or green leaves of plants and is highly safe to eat. The utility of β-carotene has already been described in Background of the Invention. In this connection, the β-carotene synthesized by the DNA sequence of the present invention in the experimental example described below had the same stereochemistry as the β-carotene present in the roots of carrot or green leaves of plants.

The gene group is typically on a plasmid as in the same manner as defined (1):

(3) A gene group used for the synthesis of zeaxanthin

One example of a gene group used for the synthesis of zeaxanthin, another yellow-orange carotenoid, comprises the aforementioned DNA sequences 1, 3, 4, 5 and 6. In other words, the DNA sequence used for the synthesis of zeaxanthin is formed by adding the DNA sequence 6 to the gene group used for the synthesis of β-carotene comprising the DNA sequences 1, 3, 4 and 5. The DNA sequences may be present on one DNA strand, or on separate multiple DNA strands individually or in groups.

In the case that a plurality of DNA sequences are present on one DNA strand, the arrangement order and direction of the aforementioned DNA sequences may be optional provided that the genetic information is expressed, i.e. the genes are in a state capable of being transcribed and translated appropriately in the host.

The biosynthetic pathway of zeaxanthin in $E.\ coli$ is explained as follows: geranylgeranyl pyrophosphate which is a substrate originally present in $E.\ coli$ is convened into phytoene by the enzyme encoded by the DNA sequence 5 the phytoene is then convened into lycopene by the enzyme encoded by the DNA sequence 4, and the lycopene is further convened into β-carotene by the enzyme encoded by the DNA sequence 3, and finally the β-carotene is convened into zeaxanthin by the enzyme encoded by the DNA sequence 6. The enzyme encoded by the DNA sequence 1 converts farnesyl pyrophosphate into geranylgeranyl pyrophosphate and thus is necessary to increase the production of lycopene (see FIG. 2).

Zeaxanthin is a xanthophyll with a color spectrum ranging from yellow to orange, and it is the yellow pigment which is present in the seed of maize and is highly safe for food. Zeaxanthin is contained in feeds for hen or colored carp and is an important pigment source for coloring them. In this connection, the zeaxanthin synthesized by the DNA sequences of the present invention in the experimental example described below had the same stereochemistry as the zeaxanthin described above.

The gene group is typically on a plasmid as in the same manner as defined in (1):

(4) A gene group used for the synthesis of zeaxanthin-diglucoside

One example of a gene group used for the synthesis of zeaxanthin-diglucoside, yet another yellow-orange carotenoid, comprises the aforementioned DNA sequences 1-6. In other words, the gene group used for the synthesis of zeaxanthin-diglucoside is formed by adding the DNA sequence 2 to the gene group used for the synthesis of zeaxanthin comprising the DNA sequences 1, 3, 4, 5 and 6. The DNA sequences may be present on one DNA strand, or on separate multiple DNA strands individually or in groups.

In the case that a plurality of DNA sequences are present on one DNA strand, the arrangement order and direction of the aforementioned DNA sequences may be optional provided that the genetic information is expressed, i.e. the genes are in a state capable of being transcribed and translated appropriately in the host.

The gene group is typically on a plasmid as in the same manner as defined in (1).

The biosynthetic pathway of zeaxanthin-diglucoside in E. coli is explained as follows: geranylgeranyl pyrophosphate which is a substrate originally present in E. coli is converted into phytoene by the enzyme encoded by the DNA sequence 5 the phytoene is then converted into lycopene by the enzyme encoded by the DNA sequence 4, and the lycopene is further converted into β-carotene by the enzyme encoded by the DNA sequence 3, the β-carotene is then converted into zeaxanthin by the enzyme encoded by the DNA sequence 6, and the zeaxanthin is finally converted into zeaxanthin-diglucoside by the enzyme encoded by the DNA sequence 2. The enzyme encoded by the DNA sequence I converts farnesyl pyrophosphate into geranylgeranyl pyrophosphate and thus is necessary to increase the production of lycopene (see FIG. 2).

Zeaxanthin-diglucoside is a carotenoid glycoside with a high water solubility which is sufficiently soluble in water at room temperature to exhibit a clear yellow color. Carotenoid pigments are generally hydrophobic and thus limited in their use as natural coloring materials in foods or the like. Zeaxanthin-diglucoside overcomes this defect. It has been isolated from edible plant saffron (Croccus sativus; Pure & Appl. Chem., 47, 121-128 (1976)), thus its safety for food apparently being continued. Zeaxanthin-diglucoside is therefore desirable as a yellow natural coloring material of foods or the like. There has been heretofore no reports with reference to the isolation of zeaxanthin-diglucoside from microorganisms.

When carotenoid pigments such as lycopene, β-carotene, zeaxanthin and zeaxanthin-diglucoside are to be produced in E. coli, the aforementioned DNA sequences 1, 4 and 5, the DNA sequences 1, 3, 4 and 5, the DNA sequences 1, 3, 4, 5 and 6, and the DNA sequences 1-6 are required, respectively. However, when a host other than E. coli, particularly one which is capable of producing carotenoids is used, it is highly possible that the host contains an intermediate compound further downstream in the carotenoid biosynthesis, so that not all of the aforementioned DNA sequences 1, 4 and 5 (for the production of lycopene), the DNA sequences 1, 3, 4 and 5 (for the production of β-carotene), the DNA sequences 1, 3, 4, 5 and 6 (for the production of zeaxanthin), or the DNA sequences 1-6 (for the production of zeaxanthin-diglucoside) may be required.

That is to say, only the DNA sequence(s) participating in the formation of the aimed carotenoid pigment from the furthest downstream intermediate compound present in the host may be necessary in these cases. Thus, when lycopene is intended to be produced in a host in which phytoene is already present, it will be sufficient to use only the DNA sequence 4 among the DNA sequences 1, 4 and 5.

It is also possible to make a host produce phytoene, a carotenoid pigment related compound, by using the DNA sequence 5 alone or, preferably, the DNA sequences 1 and 5 of the present invention.

Acquirement of DNA sequences

One method for acquiring the DNA sequences 1-6 which contain the nucleotide sequences coding for the aforementioned enzymes is the chemical polynucleotide synthesis of at least a part of their strands. However, taking into consideration that a number of nucleotides to be bonded is big, it would be more preferable than the chemical synthesis to acquire the DNA sequences from a DNA library of Erwinia uredovora 20D3 ATCC 19321 according to conventional methods in the field of genetic engineering, for example, hybridization with suitable probes.

Individual DNA sequences or a DNA sequence comprising all the DNA sequences can be obtained in these ways.

Transformant

The aforementioned gone groups comprising a combination of the DNA sequences 1-6 can be constructed using the DNA sequences obtained as described above. The DNA sequences thus obtained contain genetic information for enzymes participating in the formation of carotenoids, so that by introducing them into an appropriate host by biotechnological techniques, it will be able to obtain a transformant producing the enzymes and thus carotenoid pigments or carotenoid pigment related compounds.

(I) Host

Plants and a variety of microorganisms, as far as a suitable host-vector system is available can be transformed by a vector comprising the aforementioned DNA sequences. However, the host is required to contain farnesyl pyrophosphate which is a substrate compound of the first enzyme of the carotenoid synthesis by the DNA sequences of the present invention, or an intermediate compound further downstream from it.

It is known that farnesyl pyrophosphate is synthesized by phenyltransferases such as farnesyl pryophosphate synthetase which are common enzymes in early steps of the biosynthesis of carotenoids as well as steroids and terpenes [J. Biochcm., 72, 1101–1108 (1972)]. Accordingly, even a cell which cannot synthesize carotenoids must contain farnesyl pyrophosphate if it synthesizes steroids or terpenes. Since every cell contains at least either steroids or terpenes, theoretically almost all hosts are capable of synthesizing carotenoids using the DNA sequences of the present invention as far as a suitable host-vector system is available. Host-vector systems are known, for example, for plants such as *Nicotiana tabacura, Petunia hybrida* and the like microorganisms such as bacteria, for example *Escherichia coli, Zymornonas mobilis* and the like, and yeasts, for example *Saccharomyces cerevisiae* and the like.

(2) Transformation

It is continued here for the first time that the genetic information on the DNA sequences of the present invention can be expressed in transformed microorganisms. However, the procedures or the methods for transformation (and the production of enzymes and thus carotenoid pigments or carotenoid pigment related compounds) per se are conventional in the fields of molecular biology, cell biology or genetic manipulation, and therefore the procedures not described in detail below can be performed according to these conventional techniques.

In order to express the genes on the DNA sequences of the present invention in a host, it is necessary to insert the genes into a vector to introduce it into the host. As the vector, any of various known vectors can be used such as pBI121 or the like for plants (*Nicotiana tabacura, Petunia hybrida*); pUC19, pACYC184 or the like for *E. coli*; pZA22 or the like for *Zymomonas mobilis* (see Japanese Patent Laid-Open Publication No. 228278/87); and YEp13 or the like for yeast.

Furthermore, it is necessary to transcribe the DNA sequences of the present invention into mRNA in order to express the genes on the DNA sequences in the host. For this purpose, a promoter, a signal for the transcription, is linked to the 5'-upstream of the DNA sequences of the present invention. A variety of promoters such as CaMV35S, NOS, TR1', TR2' (for plants); lac, Tc$^r$, CAT, trp (for *E. coli*); Tc$^r$, CAT (for *Zymomonas mobilis*); ADH1, GAL7, PGK, TRP1 (for yeast) and the like can be used in the present invention.

In the case of prokaryotic hosts, it is necessary to place a ribosome-binding site (SD sequence in *E. coli*) several base-upstream from the initiation codon (ATG).

The transformation of the host with the vector thus obtained can be conducted by any appropriate method which is conventionally used in the fields of genetic manipulation or cell biology. Appropriate publications or reviews can be referenced; for example, for the transformation of microorganisms, T. Maniatis, E. F. Fritsch and J. Sambrook: "Molecular Cloning A Laboratory Manual", Cold Spring Harbor Laboratory (1982).

The transformant is identical with the used host in its genotype, phenotype or bacteriological properties except for the new trait derived from the genetic information introduced by the DNA sequence of the present invention (that is, the production of enzymes participating in the carotenoid formation and the synthesis of carotenoids or the like by the enzymes), the trait derived from the used vector, and possible losses of traits corresponding to the deletion of a part of the genetic information which might be caused by a recombination with the vector. *Escherichia coli* JM109 (pCAR1) which is an example of the transformant according to the presefit invention is deposited as FERM BP-2377.

Expression of genetic information/production of carotenoids

The transformants obtained as described above produce, mainly within the cell, enzymes participating in the carotenoid formation, and a variety of carotenoids or carotenoid pigment related compounds are synthesized by the enzymes.

Culture or the culturing condition of the transformant is essentially the same as those for the host used.

Carotenoids can be recovered by the methods, for example, illustrated in Experimental Examples 3 and 4 below.

Furthermore, enzyme proteins encoded by the DNA sequences of the present invention are produced mainly within the cell in the case of *E. coli* transformants and can be recovered by an appropriate method.

BRIEF DESCRIPTION OF THE DRAWINGS

FIGS. 1(*a*) through 1(*g*) illustrate the KpnI-HindIII fragment which was acquired from *Erwinia uredovora* 20D3 ATCC 19321 and involved in the biosynthesis of carotenoids, that is the complete nucleotide sequence of the 6918 bp DNA sequence (SEQ ID NO:13) containing the DNA sequences SEQ ID NO:1 to 6.

EXPERIMENTS

Figure 2:
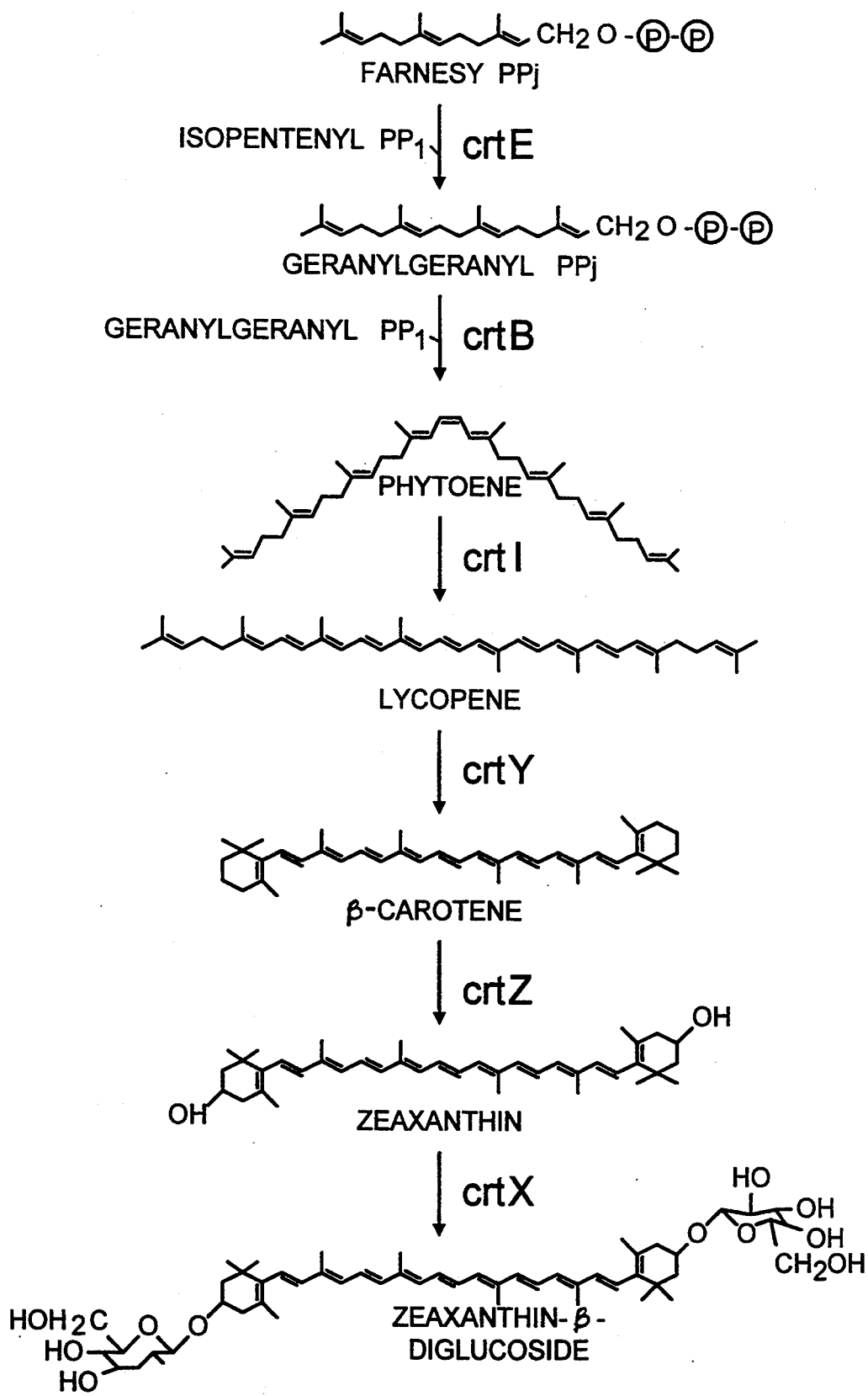
FIG. 2 illustrates the function of the polypeptides encoded by the aforementioned DNA sequences 1–6.
Figure 3:
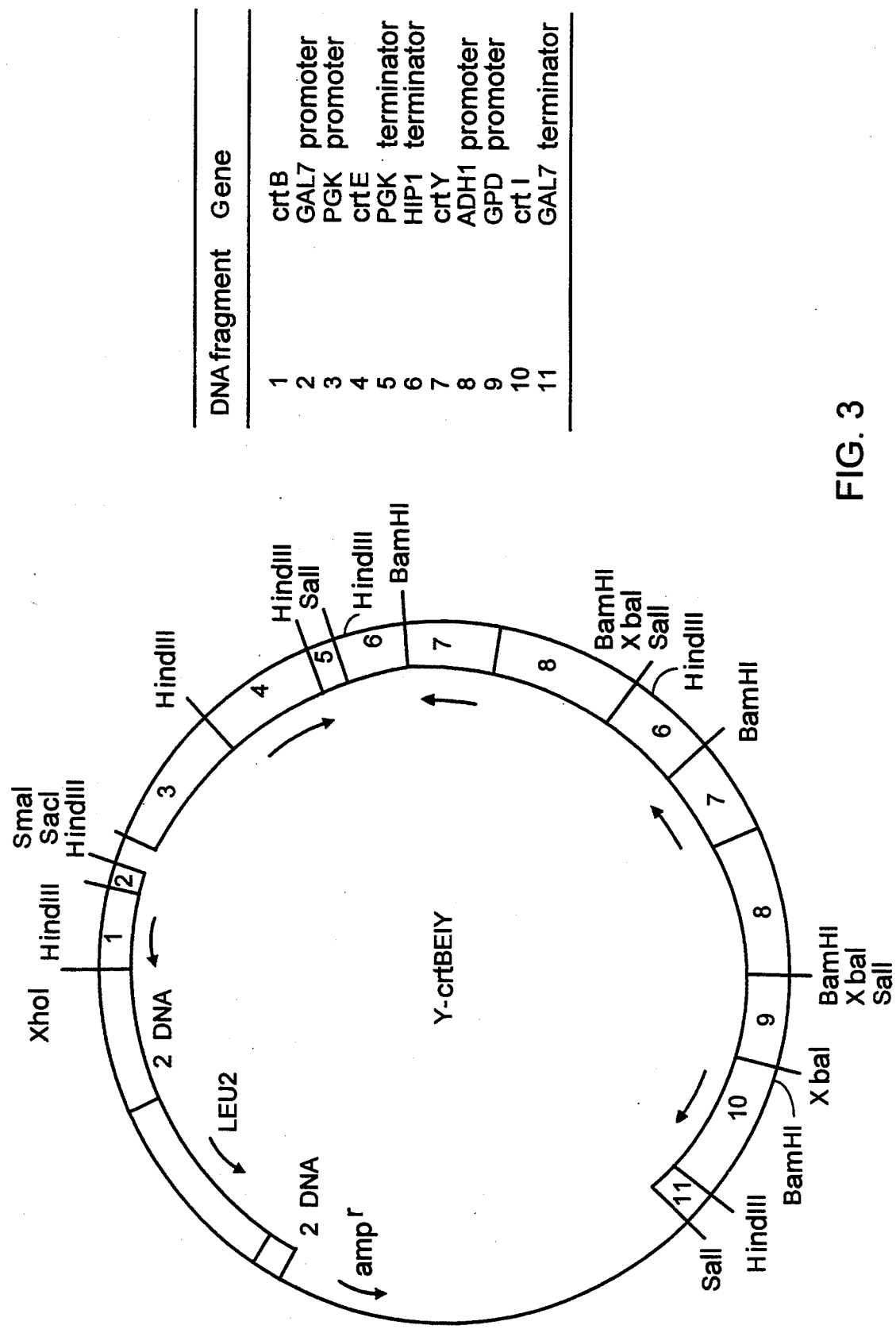
FIG. 3 illustrates the structure of vector Y-crtBEIY.

All of the strains used in the following experiments are deposited in ATCC or other deposition organizations and are freely available.

Experimental Example 1: Cloning of a gene cluster participating in the biosynthesis of a yellow pigment (referred to hereinafter as yellow pigment-synthesizing gene cluster)

(1) Preparation of total DNA

Total DNA was prepared from the cells of *Erwinia uredovora* 20D3 ATCC 19321 which had been proliferated until early-stationary phase in 100 ml of LB medium (1% tryptone, 0.5% yeast extract, 1% NaCl). Penicillin G (manufactured by Meiji Seika) was added to the culture medium to a concentration of 50 units/ml 1 hour before the harvest of the cells. The cells were harvested by centrifugation, washed with TES buffer (20 mM Tris, 10 mM EDTA, 0.1 M NaCl, pH 8), heat treated at 68° C. for 15 minutes and suspended in Solution I (50 mM glucose, 25 mM Tfis, 10 mM EDTA, pH 8) containing 5 mg/ml of lysozyme (manufactured by Seikagaku Kogyo) and 100 μg/ml of RNase A (manufactured by Sigma). The suspension was incubated at 37° C. for 30 minutes to 1 hour, and pronase E (manufactured by K. aken Seiyaku) was added to a concentration of 250 μg/ml before incubating at 37° C. for further 10 minutes. Sodium N-lauroylsarcosine (manufactured by Nacalai tesque) was added to a final concentration of 1%, and the suspension was mixed well and incubated at 37° C. for several hours. After several times of phenol/chloroform extractions, two volumes of ethanol was slowly added to recover the total DNA by winding around a glass stick. The DNA was rinsed with 70% ethanol and dissolved in 2 ml of TE buffer (10 mM Tris, 1 mM EDTA, pH 8) to give the total DNA preparation.

(2) Construction of an Escherichia coil cosmid library and acquirement of E. coli transformants producing yellow pigments 26 μg of the total DNA was incubated with I unit of a restriction enzyme Sau3AI at 37° C. for 30 minutes followed by a heat inactivation of the restriction enzyme at 68° C. for 10 minutes. Sau3AI partial digestion fragments of about 40 kb were obtained under this condition. The DNA was recovered by ethanol precipitation and a half portion was mixed with 2.5 μg of BamHI digested cosmid pJB8 treated with alkaline phosphatase and 0.2 μg of the pJB8 SalI-BamHI right arm fragment (smaller fragment) recovered by a gel electrophoresis in a total amount of 40 μl and was subjected to ligation reaction with T4 DNA ligase at 12° C. for 2 days. The cosmid pJB8 had been previously purchased from Amersham. Restriction enzymes and enzymes used for genetic manipulation were purchased from Boehringer-Mannheim, Takara Shuzo or Wako Pure Chemical Industries. The ligated DNA was used for in vitro packaging with Gigapack Gold (manufactured by Stratagene) to give phage particles sufficient for constructing a cosmid library. *Escherichia coil* DH1 (ATCC 33849) cells were infected with the phage particles, diluted to several hundred colonies per plate, and were plated on LB plates, which were cultured at 37° C. overnight and further at 30° C. for 6 hours or more. *E. coli* transformants producing yellow pigments appeared in a proportion of one colony per about 1,100 colonies. The *E. coli* transformants producing yellow pigments contained plasmids in which 33–47 kb Sau3AI partial digestion fragments were inserted into pJB8.

(3) Location of the yellow pigment-synthesizing gene cluster

One of the yellow pigment-synthesizing clones obtained above was arbitrarily chosen and its Sau3AI partial digestion fragment was subjected to another partial digestion with Sau3AI, ligated to the BamHI site of an *E. coli* vector pUC19 (purchased from Takara Shuzo), which was used to transform *Escherichia coli* JM109 (Takara Shuzo) in order to locate the yellow pigment-synthesizing gene cluster. Plasmid DNAs were prepared from 50 *E. coli* transformants producing yellow pigments which appeared on LB plates containing ampicillin, and analyzed by agarose gel electrophoresis. The smallest insert was 8.2 kb. The plasmid containing this 8.2 kb fragment was named pCAR1 and *E. coli* JM109 harboring this plasmid was named *Escherichia coli* JM109 (pCAR1). This strain produced the same yellow pigments as those of *E. uredovora*. The 8.2 kb fragment had a KpnI site near the end of the/ac promoter side and a HindIII site near the opposite end. pCAR1 was doubly digested with KpnI/HindIII (HindIII digestion was partial; the 8.2 kb fragment had two HindIII sites) and the KpnI-HindIII fragment (6.9 kb) was recovered by a gel electrophoresis and inserted between the KpnI and HindIII sites of pUC18 (this hybrid plasmid was named pCAR15). *E. coli* JM109 transformant carrying pCAR15 made a yellow colony and produced the same yellow pigments as those of *E. uredovora*. Accordingly, the genes required for the yellow pigment production were located on this KpnI-HindIII fragment (6.9 kb). In other words, the fragment carrying the yellow pigment-synthesizing genes was reduced to 6.9 kb in size.

Experimental Example 2: Analysis of the yellow pigment-synthesizing gene cluster

(1) Determination of the nucleotide sequence of the yellow pigment-synthesizing gene cluster The complete nucleotide sequence of the 6.9 kb KpnI-HindIII fragment was determined by the kilo-sequence method using a deletion kit for kilo-sequence (manufactured by Takara Shuzo) and the dideoxy method according to Proc. Natl. Acad. Sci. USA, 74 5463–5467 (1977). The KpnI-HindIII fragment containing the yellow pigment-synthesizing genes was 6918 base pairs (bp) in length and its GC content was 54%. The complete nucleotide sequence is shown in FIGS. 1(a)–(g) (SEQ ID NO:13). The nucleotides are numbered as the KpnI site being number 1.

(2) Elucidation of the yellow pigment-synthesizing gene cluster

The HindIII side of the 6918 bp DNA fragment containing the yellow pigment-synthesizing genes (the 3' side of SEQ ID NO:13) was shortened using the deletion kit for kilo-sequence. A hybrid plasmid (designated pCAR25) carrying nucleotide 1-6503 of SEQ ID NO:13 was constructed by inserting the fragment obtained by deleting from the HindIII site to nucleotide position 6504 into pUC19. *E. coli* JM109 harboring pCAR25 [referred to hereinafter as *E. coli* (pCAR25)] made a yellow colony and produced the same yellow pigments as those of *E. uredovora*. The region from the nucleotide number 6504 to 6918 in SEQ ID NO:13 was therefore not required for the yellow pigment production. The region from the nucleotide number I to 6503 containing the yellow pigment-synthesizing genes was analyzed and six open reading flames (ORFs) were found in this region. These are: an ORF from the nucleotide number 225 to 1130 coding for a polypeptide with a molecular weight of 32,583 (ORF1, A - B in FIG. 1); an ORF from the nucleotide number 1143 to 2435 coding for a polypeptide with a molecular weight of 47,241 (ORF2, C - D in FIG. 1); an ORF from the nucleotide number 2422 to 3567 coding for a polypeptide with a molecular weight of 43,047 (ORF3, E - F in FIG. 1); an ORF from the nucleotide number 3582 to 5057 coding for a polypeptide with a molecular weight of 55,007 (ORF4, G - H in FIG. 1); an ORF from the nucleotide number 5096 to 5983 coding for a polypeptide with a molecular weight of 33,050 (ORF5, I - J in FIG. 1); and an ORF from the nucleotide number 6452 to 5928 coding for a polypeptide with a molecular weight of 19,816 (ORF6, K - L in FIG. 1. This ORF6 alone has the opposite orientation with the others). Each ORF had an SD (Shine-Dalgarno) sequence complementary to the 3'-region of 16S ribosomal RNA of *E. coil* at several nucleotides upstream of its initiation codon, which strongly suggested that polypeptides were in fact synthesized in *E. coli* by these six ORFs. This was confirmed by the in vitro transcriptio-translation experiments described below.

In vitro transcription-translation analyses were carried out with the prokaryotic DNA-directed translation kit of Amersham using either ScaI-digested plasmid pCAR25 (carrying ORF1 - ORF6) or ScaI-digested plasmids carrying one of the ORFs 1-6 (with the SD sequence) as the template DNA. The later plasmids were constructed by isolating DNA fragments carrying erich ORF using appropriate restriction enzymes and inserting them into pUC18 or pUC19 in a manner that the inserted fragment would be transcribed by a read-through transcription of the lac promoter. It was confirmed that the polypeptide bands corresponding to the aforementioned respective ORFs were detected among the transcription-translation products.

All of the six ORFs were necessary for the production of the same yellow pigments as those of *E. uredovora* as described below (Experimental Example 3, 4 and 5). ORF1, ORF2, ORF3, ORF4, ORF5 and ORF6, were designated as crtE, crtX, crtY, crtI, crtB and crtZ genes, respectively. These genes were previously referred to as zexA, zexB, zexC, zexD, zexE and zexF, respectively, in the priority Japanese applications and in the US application 07/519,011 to which the present application is accorded the benefit of an earlier filing date. However, since some of these genes, namely ORFs 1, 4 and 5, have a functional similarity to locus of *Rhodobacter capsulatus*, which had been already termed as crtE, crtI and crtB locus [Molec. Gen. Genet., 216, 254–268 (1989)], the gene names have been altered accordingly after the filing of these prior applications.

(3) Analysis of homology by DNA-DNA hybridization

Total DNA of *Erwinia herbicola* Eho 10 ATCC 39368 was prepared in the same manner as in Experimental Example 1 (1). A 7.6 kb fragment containing the DNA sequence of SEQ ID NO:13 was cut out flora the hybrid plasmid pCAR1 by KpnI digestion and labeled with DNA labeling & detection kit (manufactured by Boehringer-Mannheim) by the DIG-ELISA method to give the probe DNA. Total DNAs (intact or KpnI digested) of *E. herbicola* Eho 10 ATCC 39368 and *E. uredovora* 20D3 ATCC 19321 were electrophoresed on an agarose gel and hybridized with this probe DNA using the aforementioned DNA labeling & detection kit. The probe DNA strongly hybridized with the total DNA of *E. uredovora* 20D3 ATCC 19321 but not at all with that of *E. herbicola* Eho 10 ATCC 39368. Also, the restriction map deduced from the DNA sequence of SEQ ID NO:13 was quite different from that reported in J. Bacteriol., 168, 607–612 (1986) for the *E. herbicola* DNA. It was concluded from these results that the DNA sequence of SEQ ID NO:13, that is, the DNA sequence useful for the synthesis of carotenoids according to the present invention, is not homologous with the DNA sequence containing the yellow pigment-synthesizing genes of *E. herbicola* Eho 10 ATCC 39368.

Experimental Example 3: Analysis of yellow pigments

*E. coli* (pCAR25) produced the same yellow pigments as those of *E. uredovora* 20D3 ATCC 19321 and *E. herbicola* Eho 10 ATCC 39368, and their yield was 5 times higher than that of the former and 6 times higher than that of the latter (per dry weight). Cells harvested from 8 liters of 2×YT medium (1.6% tryptone, 1% yeast extract, 0.5% NaCl) were extracted once with 1.2 liter of methanol. The methanol extract was evaporated to dryness, dissolved in methanol, and subjected to thin layer chromatography (TLC) with silica gel 60 (Merck) (developed with chloroform: methanol=4:1). The yellow pigments were separated into 3 spots having Rf values of 0.93, 0.62 and 0.30 by the TLC. The yellow (to orange) pigment at the Rf value of 0.30 which was the strongest spot was scraped off from the TLC plate, extracted with a small amount of methanol, loaded on a Sephadex LH-20 column for chromatography [30 cm×3.0 cm ($\phi$)] and developed and eluted with methanol to give 4 mg of pure products. The yellow (to orange) pigment obtained was scarcely soluble in organic solvents other than methanol and easily soluble in water, suggesting that it might be a carotenoid glycoside. This was also supported from the molecular weight of 892 by FD-MS spectrum (the mass of this pigment was larger than that of zeaxanthin (described hereinafter) by the mass of two glucose molecules). When this substance was hydrolyzed with 1N HCl at 100° C. for 10 minutes, zeaxanthin was obtained. Accordingly, the pigment was analyzed by acetylation according to the usual method. A large excess of acetic anhydride was added to the pigment dissolved in 10 ml of pyridine and the mixture was stirred at room temperature and left standing overnight. After the completion of reaction, water was added to the mixture and chloroform extraction was carried out. The chloroform extract was concentrated and loaded on a silica gel column [30 cm ×3.0 cm ($\phi$)] and the pigment was eluted with chloroform. The pigment gave a $^1$H-NMR spectrum identical with the tetraacetyl derivative of zeaxanthin-$\beta$-diglucoside [Helvetica Chimica Acta, 57, 1641–1651 (1974)], identifying itself as zeaxanthin-$\beta$-diglucoside (its structure being illustrated below).

The yield of the pigment was 1.1 mg/g dry weight. It had a solubility of at least 2 mg in 100 ml of water and methanol, water being a better solvent than methanol. It had low solubilities in chloroform and acetone; it dissolved only 0.5 mg in 100 ml of these solvents.

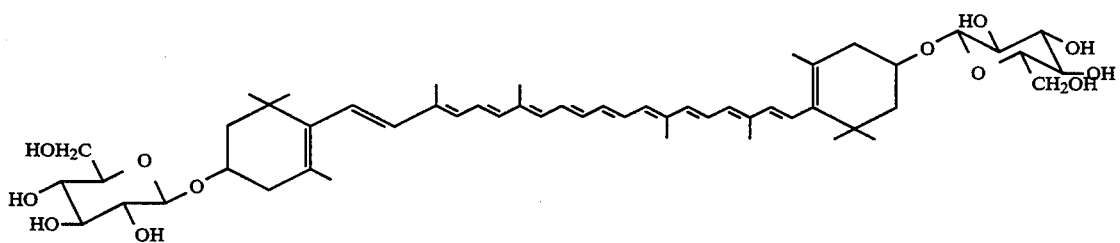

Experimental Example 4: Analysis of the metabolic intermediates of carotenoids (1) Construction of various deletion plasmids A hybrid plasmid (designated as pCAR16) was constructed by inserting the 1-6009 fragment of SEQ ID NO:13, which was obtained by deletion to nucleotide position 6010 from the HindIII site (the 3' end) of the 6918 bp fragment containing the yellow pigment-synthesizing genes (DNA sequence SEQ ID NO:13) using deletion kit for kilo-sequence. pCAR16 contains genes crtB, E, I, X, and Y. Various deletion plasmids were constructed, as shown in Table 1, based on pCAR16 and the aforementioned hybrid plasmid pCAR25 (containing all the six genes).

TABLE 1

| Plasmid | Construction method | ORFs (genes) functioning |
|---|---|---|
| pCAR25 | see text | 1–6<br>crtE crtB crtI crtY<br>crtZ crtX |
| PCAR25delB | Frame shift in BstEII (1235) of pCAR25 | 1, 3–6<br>crtE crtB crtI crtY<br>crtZ |
| pCAR16 | see text | 1–5<br>crtE crtB crtI crtY<br>crtX |
| pCAR16delB | Frame shift in BstEII (1235) of pCAR16 | 1, 3–5<br>crtE crtB crtI crtY |
| pCAR16delC | Frame shift in SnaBI (3497) of pCAR16 | 1, 2, 4, 5<br>crtE crtB crtI crtX |
| pCAR-ADE | Deletion of the BstEII (1235)- SnaBI (3497) fragment from pCAR16 | 1, 4, 5<br>crtE crtB crtI |
| pCAR-ADEF | Deletion of the BstEII (1235)- SnaBI (3497) fragment from pCAR25 | 1, 4–6<br>crtE crtB crtI crtZ |
| pCAR25delD | Frame shift in BamHI (3652) of pCAR25 | 1–3, 5, 6<br>crtE crtB crtY crtZ<br>crtX |
| pCAR-AE | Deletion of the BstEII (1235)- BamHI (3652) fragment from pCAR16 | 1, 5<br>crtE crtB |
| pCAR-A | Insertion of the KpnI (1)- BstEII (1235) fragment in pUC19 | 1<br>crtE |
| pCAR-E | Insertion of the Eco52I (4926)- 6009 fragment in pUC19 | 5<br>crtB |
| pCAR25delE | Frame shift in MluI (5379) of pCAR25 | 1–4, 6<br>crtE crtI crtY crtZ<br>crtX |
| pCAR25delA | Frame shift in AvaI (995) of pCAR25 | 2–6<br>crtB crtI crtY crtZ<br>crtX |
| pCAR-CDE | Insertion of the SalI (2295)- 6009 fragment in pUC19 | 3–5<br>crtB crtI crtY |

The number within parentheses behind the name of respective restriction enzymes represents the number of the first nucleotide of its recognition site. The nucleotide numbers correspond to those in FIG. 1 and SEQ ID:NO:13. Analyses of metabolic intermediates of the carotenoid synthesis were performed using E. coli JM109 transformed with these deletion plasmids [referred to hereinafter as E. coli (name of plasmid)].

(2) Identification of zeaxanthin

The cells of E. coli (pCAR25de1B) (exhibiting orange) harvested from a 3 liter culture in 2×YT medium were extracted twice with 400 ml portions of acetone at low temperature, concentrated, then extracted with chloroform:methanol (9:1) and evaporated to dryness. The extract was dissolved and subjected to silica gel column chromatography [30 cm×3.0 cm ($\phi$)]. After the column was washed with chloroform, an orange band was eluted with chloroform:methanol (100:1). This pigment was dissolved in ethanol, recrystallized at low temperature to give 8 mg of pure products. Analyses by its UV-visible absorption, $^1$H-NMR, $^{13}$C-NMR and FD-MS (m/e 568) spectra revealed that this substance had the same planar structure as zeaxanthin ($\beta,\beta$-carotene-3,3'-diol). It was then dissolved in diethyl ether: isopentane: ethanol (5:5:2), and the CD spectrum was measured. As a result, it was found that this substance had a 3R,3'R-stereochemistry [Phytochemistry, 27, 3605–3609 (1988)]. Therefore, it was identified as zeaxanthin ($\beta,\beta$-carotene-3R,3'R-diol), whose structure is illustrated below. The yield was 2.2 mg/g dry weight. This substance corresponded to the yellow pigment having an Rf value of 0.93 in Experimemal Example (1).

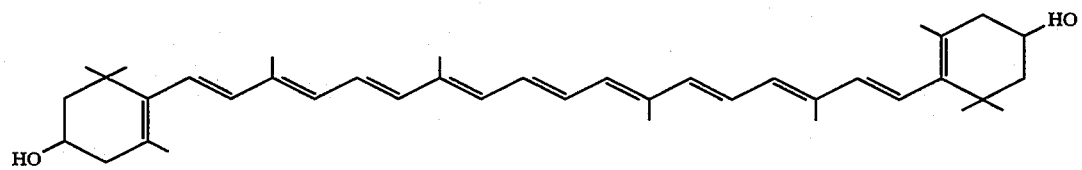

(3) Identification of $\beta$-carotene

The cells of E. coli (pCAR16) (exhibiting orange) harvested from a 3 liter culture in LB medium were extracted 3 times with 500 ml portions of cold methanol at low temperature and the methanol extract was further extracted with 1.5 liter of hexane. The hexane layer was concentrated and subjected to silica gel column chromatography [30 cm×3.0 cm ($\phi$)]. Development and elution were conducted with hexane:ethyl acetate (50:1) to collect an orange band. The orange fraction was concentrated and recrystallized from ethanol to give 8 mg (reduced weight without moisture) pure products. This substance was presumed to be $\beta$-carotene from its UV-visible absorption spectrum, and the molecular weight of 536 by FD-MS spectrum also supported this presumption. Upon comparing this substance with an authentic sample (Sigma) of $\beta$-carotene by $^{13}$C-NMR spectrum, all the chemical shifts of carbons were identical. Thus, this substance was identified as β-carotene (all-trans-β,β-carotene, whose structure was illustrated below). It was also confirmed by a similar method that *E. coli* (pCAR16delB) accumulated the weight) of the total carotenoid yield in a hyperproduction mutant of carrot (Kintokininjin) culture cells described in Soshikibaiyou (The Tissue Culture), 13, 379–382 (1987).

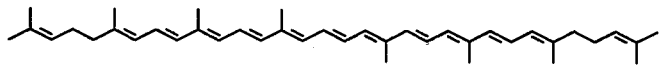

same β-carotene as described above. Its yield was 2.0 mg/g dry weight, which corresponded to 2–8 times (per dry weight) of the total carotenoid yield in carrot (Kintokininjin) cultured cells described in Soshikibaiyou (The Tissue Culture), 13, 379–382 (1987).

(5) Identification of phytoene

The cells of *E. coli* (pCAR-AE) were harvested from a 1.5 liter culture in 2×YT medium were extracted twice with 200 ml portions of acetone, concentrated,

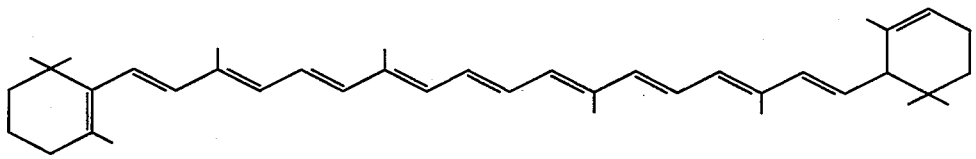

(4) Identification of lycopene

The cells of *E. coli* (pCAR16delC) (exhibiting red) harvested from a 3 liter culture in LB medium were extracted once with 500 ml of cold methanol at low temperature, and the precipitate obtained by centrifugation was extracted again with 1.5 liter of chloroform. The chloroform layer was concentrated and subjected to silica gel chromatography [30 cm×3.0 cm (φ)]. Development and elution were conducted with hexane:chloroform (1:1) to collect a red band. This fraction was concentrated. This substance was presumed to be lycopene from its UV-visible absorption spectrum, and the molecular weight of 536 by FD-MS spectrum also supported this presumption. Upon comparing this substance with the authentic sample (Sigma) of lycopene by ¹H-NMR spectrum, all of chemical shifts of hydrogens were identical. When, this substance and the authentic sample were subjected to TLC with silica gel 60 (Merck) [developed with hexane:chloroform (50:1)] and with RP-18 [developed with methanol:chloroform (4:1)], the displacement distances of these samples were completely equal to each other. Thus this substance was identified as lycopene (all-trans-ψ,ψ-carotene, whose structure was illustrated below). It was also confirmed by a similar method that *E. coli* (pCAR-ADE) and *E. coli* (pCAR-ADEF) accumulated the same lycopene as described above. The yield of the former was 2.0 mg/g dry weight, which corresponded to 2 times (per dry extracted twice with 100 ml portions of hexane, and evaporated to dryness. This was subjected to silica gel chromatography [30 cm×3.0 cm (φ)]. Development and elution were conducted with hexane:chloroform (1:1) to collect a band which had a strong UV absorption, and it was confirmed to be phytoene by its UV absorption spectrum. It was further subjected to Scphadex LH-20 column (Pharmacia) chromatography [30 cm×3.0 cm (φ)]. Development and elution were conducted with chloroform:methanol (1:1) to give 4 mg of pure products. The comparison of the ¹H-NMR spectrum of this substance with the ¹H-NMR spectra of trans- and cis-phytoene (J. Magnetic Resonance, 10, 43–50 (1973)) showed this substance to be a mixture of the trans- and cis-isomers. Isomerization from trans-isomer to cis-isomer hardly occurs, and thus it was judged that such a mixture was produced as a result of cis-trans isomerization in the course of the purification. It was therefore concluded that the original phytoene was the cis-type phytoene (15,15'-cis-phytoene, whose structure was shown below). It was also confirmed by a similar method that *E. coli* (pCAR25delD) accumulated the same phytoene as described above.

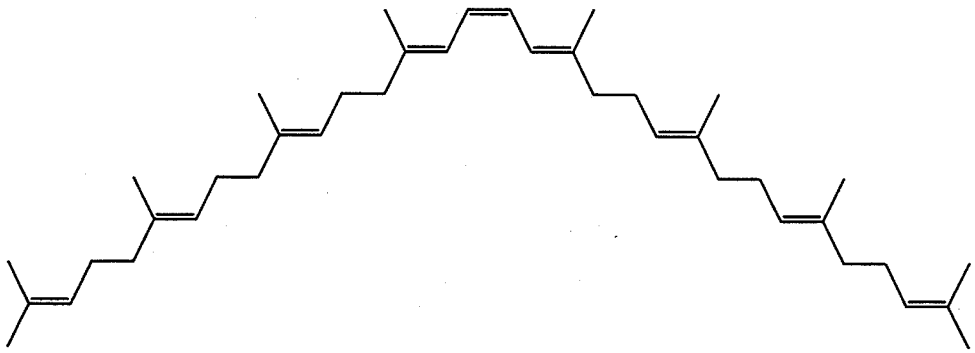

Experimental Example 5: Identification of carotenoid biosynthesis genes

From the facts that *E. coli* (pCAR25) produced zeaxanthin-diglucoside and that *E. coli* (pCAR25delB) harboring a plasmid in which crtX had been removed from pCAR25 accumulated zeaxanthin, it was found that the crtX gene encoded the glycosylation enzyme which was capable of convening zeaxanthin into zeaxanthin-diglucoside. Similarly, from the fact that E. coli (pCAR16delB) harboring a plasmid in which crtZ had been removed from pCAR25delB accumulated β-carotene, it was found that the crtZ gene encoded the hydroxylation enzyme which was capable of convening β-carotene into zeaxanthin. Similarly, from the fact that the E. coil (pCAR-ADE) harboring a plasmid in which crtY had been removed from pCAR16delB accumulated lycopene, it was found that the crtY gene encoded the cyclization enzyme which was capable of convening lycopene into β-carotene. E. coli (pCAR-ADEF) carrying both of the crtE, crtI and crtB genes required for producing lycopene and the crtZ gene encoding the hydroxylation enzyme synthesized only lycopene. This demonstrates directly that the hydroxylation reaction in carotenoid biosynthesis occurs after the cyclization reaction. Further, from the facts that E. coli (pCAR-ADE) accumulated lycopene and that E. coli (pCAR-AE) harboring a plasmid in which the crtI gene had been removed from pCAR-ADE accumulated phytoene, it was found that the crtI gene encoded the desaturation enzyme which was capable of convening phytoene into lycopene. E. coli (pCAR-A) carrying only the crtE gene and E. coli (pCAR-E) carrying only the crtB gene were not able to produce phytoene. These results indicate that both the crtE and crtB genes were required for producing phytoene in E. coli.

A 3 ml overnight culture of E. coli JM101 (pCAR-A) or E. coli JM101 (pCAR-E) was inoculated to 50 ml LB medium and was further grown at 37° C. for 3 hours. The cells were harvested and resuspended in 1 ml of 0.1 M Tris-HCl (pH 8.0) and broken by a French press at a pressure of 500 bar. The suspension was treated with DNase (20 μg/ml) for 15 minutes on ice, centrifuged at 10,000 g for 3 minutes, and the supernatant was assayed for geranylgeranyl pyrophosphate (GGPP) synthase activity. The assay mixture contained in 0.5 ml: 5 μmol ATP, 3 μmol MnCl$_2$, 2 μmol MgCl$_2$, 20,000 dpm of trans,trans-2-$^{14}$C-farnesyl pyrophosphate (FPP, specific activity 1.88 GBq/mmol; purchased from Amersham), and 400 μl of the supernatant. The mixture was incubated at 30° C. for two hours and then HCl was added to a final concentration of 2 M to hydrolyze the prenyl pyrophosphates in the mixture into their alcohols. After keeping the mixture at room temperature for 30 minutes, the prenyl alcohols were extracted by hexane containing 10% diethylether and separated by HPLC with a Spherisorb ODS-1 5μg, 25 cm column (Phase Separations Ltd.) using 10% (v/v) water in methanol as the solvent at a flow rate of 1 ml/min. Radioactivity in the eluent was determined on-line with a radioactivity monitor. In vitro GGPP synthase activity was calculated as the percentage of radioactivity in GGPP vs. the sum of radioactivity in FPP and GGPP. As shown in Table 2, E. coli strains carrying the crtE gone (pCAR25 and pCAR-E) had an elevated activity to convert FPP into GGPP, which indicates that crtE encodes GGPP synthase.

TABLE 2

| E. coli strain | Radioactivity (dpm) in: | | Conversion (%) |
|---|---|---|---|
| | FPP (substrate) | GGPP (product) | |
| JM101 (pCAR25) | 8083 | 12814 | 61.5 |
| JM101 (pCAR-E) | 18274 | 75 | 0.4 |
| JM101 (pCAR-A) | 12427 | 7064 | 36.2 |

TABLE 2-continued

| E. coli strain | Radioactivity (dpm) in: | | Conversion (%) |
|---|---|---|---|
| | FPP (substrate) | GGPP (product) | |
| JM101[a] | 21685 | 875 | 3.8 |

[a] non-transformant as a control

The activity of the reaction next to GGPP synthesis in carotenoid biosynthesis, the conversion of GGPP into phytoene, was assayed for the E. coli strains in Table 2 in a similar manner, but for some unknown reason the activity was not detected for any of the strains. Therefore, two plasmids for transforming Agrobacterium tumefaciens containing only either crtB or crtE gene were constructed by inserting either the Eco52I (4926) - EcoRI (6009) fragment or the KpnI (1) - BstEII (1235) fragment from the DNA sequence of SEQ ID NO:13, respectively, into the filled-in StnaI-SstI large fragment of a binary vector pBI121 (Clontech). The resultant plasmids, pBICRT-B and pB[CRT-E], had the β-glucuronidase gene replaced by respective crt genes. A. tumefaciens LBA4404 transformants carrying either of these plasmids were grown overnight at 28° C. in a 10 ml medium containing yeast extract 5 g/l, tryptone 20 g/l, MgSO$_4$·7H$_2$O 10 g/l, adjusted to pH 7.5. The culture was inoculated into 50 ml of the same fresh medium and grown for further 4 hours, and the cells were harvested and resuspended in 1 ml of 0.1 M Tris-HCl pH 8.0. The cells were broken by a French press at 500 bar, treated with DNase (20 μg/ml) for 15 minutes on ice, and assayed for phytoene synthase activity. The assay mixture contained in 0.5 ml: 5 μmol ATP, 3 μmol MnCl$_2$, 2 μmol MgCl$_2$, 500,000 dpm of R-2-$^{14}$C-mevalonic acid (specific activity 56.7 mCi/nmol; purchased from Amersham), 200 μl of a Fttsarium SG4 extract, and 200 μl of the cell homogenate. The Fusarium extract, which converts the $^{14}$C-mevalonic acid into $^{14}$C-GGPP, was prepared as described by Sandmann and Albrecht [Z. Naturforsch., 45c, 487–491, (1990)]. After incubating at 30° C. for two hours, 2.5 ml of methanol containing 6% (v/v) KOH was added and the lipids in the assay mixture were saponified at 65° C. for 15 minutes in the dark, and non-saponifiable lipids were extracted with hexane containing 10% diethylether and analyzed by HPLC as in the GGPP synthase assay described above except that the solvent used was acetonitrile:methanol:2-propanol (85:10:5, v/v).

In the assay mixture containing the homogenate of A. tumefaciens (pBICRT-B), radioactive 15-cis as well as all-trans phytoene were detected, which indicates crtB encodes phytoene synthase that can convert GGPP directly into phytoene. The homogenate of A. tumefaciens (pBICRT-E) was not able to form phytoene. From these analyses described above, all of the six crt genes have been identified and the biosyhthetic pathway of carotenoids have also been clear. These results are listed in FIG. 2.

E. coli (pCAR25delE) accumulated no detectable carotenoid intermediate, while E. coli (.pCAR25delA) and E. coli (pCAR-CDE) were able to produce a small amount of carotenoids. That is to say, E. coli (pCAR25delA) and E. coli (pCAR-CDE) produced 4% of zeaxanthin-diglucoside and 2% of β-carotene as compared with the E. coli (pCAR25) and the E. coli (pCAR16delB), respectively. These results are consistent with the observation that E. coli without any crt genes was capable of synthesizing GGPP at a low level (see Table 2). It is not clear at this moment, however, why phytoene was not detected in *E. coli* (pCAR-E) carrying the crtB gene.

As described above, in the present invention the detailed biosynthetic pathway of carotenoids including general and famous carotenoids such as lycopene, β-carotene and zeaxanthin and a water soluble carotenoid zeaxanthin-diglucoside were for the first time elucidated, and a gene cluster useful for their biosynthesis was obtained for the first time. In this connection, lycopene, β-carotene and zeaxanthin which were produced by the genes in the aforementioned Experimental Examples were stereochemically identical with those derived from higher plants [T.W. Goodwin: "Plant Pigments", Academic Press (1988)].

Zeaxanthin-diglucoside has been isolated from a plant [Pure & Appl. Chem., 47, 121-128 (1.976)] but its isolation from microorganisms has not been reported before.

Experimental Example 6: Synthesis of carotenoids in Zymomonas

*Zymomonas mobilis* is a facultative anaerobic ethanol-producing bacterium. It has a higher ethanol producing rate than yeast (*Saccharomyces cerevisiae*), so that it is preferable as a fuel alcohol-producing bacterium in future. Zymomonas has a special metabolic pathway, Entner-Doudoroff pathway, instead of the glycolytic pathway, and do not produce carotenoids. In order to add further values to this bacterium, the carotenoid biosynthesis genes were introduced into Zymomonas.

The 7.6 kb fragment containing the DNA sequence of SEQ ID NO:13 was cut out from the hybrid plasmid pCAR1 by KpnI digestion and treated with DNA polymerase I (Klenow enzyme). The fragment thus treated was ligated to the EcoRV site of the cloning vector pZA22 for Zymomonas [see Agric. Biol. Chem., 50, 3201-3203 (1986) and Japanese Patent Laid-Open Publication No. 228278/87] to construct a hybrid plasmid pZACAR1. Similarly, the 1-6009 fragment of the DNA sequence SEQ ID N0:13 was cut out from pCAR16 by KpnI/EcoRI digestion and treated with DNA polymerase I (Klenow enzyme). The fragment thus treated was ligated to the EcoRV site of pZA2,2 to construct a hybrid plasmid pZACAR16. The orientation (as in SEQ ID NO:13) of the inserted fragments in these plasmids was opposite to the orientation of the Tc$^r$ gene. These plasmids were introduced into *Z. mobilis* NRRL B-14023 by conjugal transfer with the helper plasmid pRK2013 (ATCC 37159) and stably maintained in this strain. *Z. mobilis* NRRL B-14023 in which pZACA. R1 or pZACAR16 had been introduced formed a yellow colony and produced zeaxanthin-diglucoside in an amount of 0.28 mg/g dry weight or β-carotene in an amount of 0.14 mg/g dry weight, respectively. Carotenoids were thus successfully produced in Zymomonas by the carotenoid biosynthesis genes of the present invention.

Experimental Example 7: Synthesis of β-carotene and lycopene in Saccharomyces cereviceae Saccharomyces is a yeast widely utilized for fermentation and bakery. No natural species of this yeast is reported to synthesize carotenoids. In the following experimental example, the DNA sequences 1, 3, 4 and 5 of the present invention were introduced and expressed in *Saccharomyces cereviceae* to produce β-carotene and lycopene in the transformants.

(1) Isolation of yeast promoters and terminators

GAL7 promoter and terminator

The genomic DNA of *Saccharomyces cereviceae* RC7 (αleu2 ura3 trp1) was partially digested with Sau3AI into about 10 kb fragments and inserted into the BamHI site of pBR322 to construct a yeast genomic DNA library. A clone containing the GAL7 gene was obtained from this library by screening with a 21mer synthetic oligonucleotide probe complementary to the nucleotide 1-21 of the coding sequence of the GAL7 gene [Molec. Cell. Biol., 6, 246-256 (1986)]. The genomic DNA fragment in this clone was partially digested with Sau3AI into about 600 bp fragments and subcloned into PUC19. A clone containing the GAL7 promoter fragment was obtained using the same 21mer probe described above. The 5' upstream of the promoter fragment was deleted up to about 270 bp upstream of the transcription start by exonuclease III (Takara Shuzo, Co.) and a BamHI linker was added there. Similarly, the 3' downstream of the promoter fragment was deleted up to 6 bp upstream of the transcription start and a BglII linker was added. The 300 bp BamHI-BglII fragment thus obtained, which contained the GAL7 promoter, was inserted between the BamHI and BglII sites of a yeast expression vector YEp13K (European patent application 339 532; referred to as EP 339 532 below). The resultant plasmid was linearized with BglII, filled in with the Klenow fragment and self-ligated after the addition of a HindIII linker to construct the plasmid pGAL7pro.

A clone containing the GAL7 terminator was obtained from the PUC19 subclone library described above by screening with a 30mer synthetic probe complementary to the nucleotide sequence 30 bp upstream of the stop codon of GAL7. A 420 bp HindIII-SalI fragment containing the terminator was excised from this clone and inserted between the HindIII and SalI sites of pUC19 to construct the plasmid pGAL7term.

PGK promoter

Another yeast genomic library was constructed in the same manner as described above from the genomic DNA of *Saccharomyces cereviceae* S288C ATCC 26108. A clone containing the PGK gene was obtained from this library by screening with a 28mer synthetic oligonucleotide probe complementary to the nucleotide 1-28 of the coding sequence of the PGK gene [Nucleic Acids Res., 10, 7791 (1982)]. A 2.9 kb fragment containing the PGK gene was obtained from the plasmid in this clone by HindIII digestion and was inserted into pUC19. The 2.3 kb HindIII-SalI fragment containing the PGK promoter and the first half of the coding sequence was isolated from this plasmid and inserted between the HindIII and SalI sites of pBR322 to construct pBRPGK. A series of deletions were constructed by an exonuclease III digestion of the SalI-linearized pBRPGK. The digested DNA was filled in with the Klenow fragment, ligated with HindIII linkers, digested with HindIII, and cloned into the HindIII site of pUC19. A plasmid carrying a PGK fragment deleted up to 7 bp upstream of the transcription start was selected. This plasmid was partially digested with HindIII to cut only the site upstream of the PGK promoter, filled in with the Klenow fragment and self-ligated after the addition of a BglII linker to construct the plasmid pPGKpro.

Plasmid pPG2 (EP 339 532), which carries the PGK terminator, was cut with SmaI, ligated with HindIII linkers and digested with HindIII and SalI to isolate the 0.38 kb HindIII-SalI fragment containing the PGK terminator. This fragment and the 1.6 kb BglII-HindIII fragment containing the PGK promoter excised from pPGKpro were ligated between the BglII and SalI sites of YEp13K to obtain an expression vector Y-PGK-PT.

HIP1 terminator

A clone containing the HIP1 gene was obtained from the S288C genomic library described above by screening with a 30met synthetic oligonucleotide probe complementary to the nucleotide 46-75 of the coding sequence of the HIP1 gene [Gene, 38, 205-214 (1985)]. A 1 kb fragment containing the HIP1 terminator was isolated from the plasmid in this clone with BamHI and SalI and was inserted between the BamHI and SalI sites of pBR322 to construct the plasmid pHIPT.

(2) Construction of crt gene expression units crtB pCAR16 was digested with Eco52I, filled in with the Klenow fragment, digested with EcoRI and the 1083 bp (Eco52I)-EcoRI fragment containing the crtB gene was isolated. (Eco52I) represents a filled in Eco52I site. In the following document, parenthesized restriction sites represent the filled in sites. pUC19 was cut with SphI, filled in and digested with EcoRI. The (Eco52I)-EcoRI fragment containing the crtB gene was ligated between the (SphI) and EcoRI sites of pUC].9 thus obtained to construct a plasmid pcrtB. The 901 bp TaqI-EcoRI fragment containing the most part of the crtB gene was excised from pcrtB and ligated between the SphI and EcoRI sites of M13mp18 (Takara Shuzo Co.) together with the synthetic oligonucleotide fragment shown below to construct mp18-crtB.

5' GCAGTTGGCT 3'(SEQ ID NO:14)
3' GTACCGTCAACCGAGC 5' (SEQ ID NO:15)

mp18-crtB was cut with EcoRI, filled in with the Klenow fragment and self-ligated after the addition of a XhoI linker to obtain mp18-crtBXhoI. A BamHI-HindIII fragment containing the GAL7 promoter was excised from the plasmid pGAL7pro described in above (1), and the HindIII-XhoI fragment containing the crlB gene was excised from mp18-crtBXhoI. These fragment were together ligated between the BglII and XhoI sites of YEp13K to construct Y-GAL7-crtB, on which the GAL7 promoter is linked to the 5' of the crIB gene via the HindIII site.

crtI

The 1.87 kb SnaBI-EcoRV fragment containing the crtI gene was excised from pCAR16 and inserted between the (SphI) and SmaI sites of pUC18 to construct pcrtI. The orientation of the crtI gene on pcrtI was such that the EcoRI and HindIII sites of pUC18 were upstream and downstream, respectively, of the gene. pcrtI was linearized with HindIII and about 200 bp sequence was deleted with exonuclease III. After ligating HindIII linkers, the 1.7 kb EcoRI-HindIII fragment containing the crtI gene was isolated and inserted between the EcoRI and HindlH sites of pUC18 to construct pcrtId. A XbaI site was created at 18 bp upstream of the transcription start of crtI on pcrtld by an in vitro mutagenesis [Bio/Technology, 2, 636-639 (1984)] using a synthetic oligonucleotide shown below to obtain pcrtIXbaI.

5' ACGACTCATCTAGAAGGAGCGACTAC 3'
( SEQ ID NO: 16 )

The 1.0 kb XhoI-(HindIII) fragment containing the GPD promoter was excised from a yeast expression vector pAX50F2 (lip 339 532), and the (XbaI)-HindIII containing the crtI gene was excised from pcrtIXbaI. These fragments were together ligated between the XhoI and HindIII sites of Bluescript II SK(+) (Stratagene) to construct pGPD-crtI. A unique SalI site is conveniently located upstream of the GPD promoter on pGPD-crtI. A SalI-HindIII fragment containing the GPD promoter-crtI gene was excised accordingly, and a HindIII-SalI fragment containing the GAL7 terminator was excised from the plasmid pGAL7term described in above (1). These fragments were together inserted in the SalI site of pUC19 to obtain pGPD-crtIT, on which the GPD promoter is linked to the 5' of the ertI gene via the XbaI site and the GAL7 terminator to the 3' via the Hitcliff site.

crtE

The 1.1 kb SpeI-PvuI fragment containing the crtE gene was excised from pCAR16 and made blunt-ended with mung bean nutlease, and inserted into the filled in XbaI site of pUC19 to construct portE. The orientation of the crtE gene on pcrtI was such that the EcoRI and SaIt sites of pUC19 were upstream and downstream, respectively, of the gene. pcrtE was digested with SacI and BamHI, treated with mung bean nuclcase to delete the sequence up to 9 bp upstream of the crtE coding region, and self-ligated. The 0.94 kb EcoRI-SalI fragment containing the crtE gene was excised from this plasmid, made blunt-ended with mung bean nuclease, and inserted into the HindIII site of pUC19 after the addition of a HindIII linker to obtain pcrtE-H. The 0.94 kb HindIII fragment containing the crtE gene was excised from pcrtE-H and inserted into the HindIII site of the expression vector Y-PGK-PT described above to construct Y-crtE, on which the PGK promoter is linked to the 5' and the PGK terminator to the Y of the crtE gene via the HindIII site.

crtY

The 1.3 kb EcoRV-BamHi fragment containing the crtY gene was excised from pCAR16 and inserted between the SmaI and BamHI sites of pUC19 to construct pettY. The 1190 bp NruI-BamHI fragment containing the most part of the crtY gene was excised from pcrtY and ligated into the BamHI site of pUC19 together with the synthetic oligoDNA fragment shown below to construct pcrtY-BS.

5' GATCCCCGGGAGCGGCTATGCAACCGCATTATGATCTGATTCTCG
3'       GGGCCCTCGCCGATACGTTGGCGTAATACTAGACTAAGAGC

TGGGGGCTGGACTCG 3' (SEQ ID NO:17)
ACCCCCGACCTGAGC 5' (SEQ ID NO:18)

pcrtY-BS has a new SmaI site 13 bp upstream of the transcription start of the crtY gene. The 1.2 kb SmaI-BamHI fragment containing the crtY gene was excised from pcrtY-BS, and the 1.5 kb BamHI-(HindIII) fragment containing the ADH1 promoter was excised from a plasmid pYADH (EP 339 532) carrying the promoter. These fragments were together ligated into the BamHI site of pUC19 to obtain pADH-crtY. The orientation of the crtY gene on pADH-crtY was such that the SalI site of pUC19 was upstream of the ADH1 promoter. The 2.7 kb SalI-BamHI fragment containing the ADH1 promoter-crtY gene was excised from pADH-crtY and the BamHI-SalI fragment containing the HIP1 terminator was excised from the plasmid pHIPT described in above (1). These fragments were ligated into the SalI site of pUC19 to obtain 19-crtY, on which the ADH1 promoter is linked to the 5' of the crt[gene and the HIP1 terminator is linked to the Y via the BamHI site.

(3) Construction of the vector

A vector plasmid Y-crtBEIY for conferring the ability of carotenoid (such as β-carotene and lycopene) synthesis to yeast was constructed as follows.

The BamHI-XhoI fragment containing the GAL7 promoter-criB gene was excised from Y-GAL7-crtB and inserted between the BglII and XhoI sites of Y-crtE to obtain Y-crtBE. Then, the SalI fragment containing the GPD-promoter-crtI gene-GAL7 terminator was excised from pGPD-crtIT and inserted into the SalI site of Y-crtEB to obtain Y-crtEBI. Finally, the SalI fragment containing the ADH1 promoter-crtY gene-HIP1 terminator was excised from 19-crtY and ligated with Y-crtEBI partially digested with SalI to obtain Y-crtBEIY as shown in FI. The plasmid has the LEU2 gene as a selection n (4) Production of carotenoids in yeast In Y-crtBEIY, the criB, E, I and Y genes are regulated by the GAL7, PGK, GPD and ADH1 promoters, respectively. Of these four promoters, the GAL7 promoter is a galaclose inducible promoter and the others are constitutive ones. Accordingly, in order to express all the four promoters at the same time, it is necessary to add galactose to the culturing medium. The yeast strain to be transformed should therefore be able to grow well on a medium containing galactose. One example of such yeast strain is *Saccharomyces cereviceae* RC7 (ct leu2 ura3 trpl), which was used as the host in the following experiment.

Y-crtBEIY was introduced to the yeast strain by the lithium method [J. Bacteriol., 153, 163 (1983)] and transformants were selected on a medium without leucine. One transformant was arbitrarily chosen and designated as BCAR1. BCAR1 was cultured for 3 days at 30° C. in 200 ml of a selective medium SG-Leu containing galactose [0.67% amino acid-free yeast nitrogen base (Difco), 2% galactose, 20 mg/l arginine-HCl, 20 mg/l histidine-HCl, 30 mg/l isoleucine, 30 mg/l lysine-HCl, 20 mg/l methionine, 50 mg/l phenylalanine, 200 mg/l threonine, 30 mg/l tyrosine, 20 mg/l tryptophan, 20 mg/l adenine sulphate, 20 mg/l uracil, pH 5.8]. Carotenoids were extracted from the yea-st according to Johnson, E.A. et aL [J. Gen. Microbiol., 115, 173–183 (1979)]. The harvested cells were broken with glass beads and the carotenoids were extracted by shaking with a twenty volume of acetone. The acetone extract (60 ml) was filtered and the carotenoids were extracted twice with 25 ml of hexane. After extracting water- soluble impurities by shaking with 25 ml of water for five times, the hexane layer was dehydrated, concentrated and evaporated to dryness. The carotenoids were dissolved in a small volume of chloroform and analyzed with HPLC using a Nova-pak HR $C_{186}\mu$ column (3.9×300 mm; Waters). The carotenoids were eluted with acetonitrile:methanol:2-propanol (90:6:4) at a flow rate of 1 ml/min. Synthetic all-trans-β,β-carotene (Sigma) and lycopene from tomato (purchased from Sigma) were used as standards. Upon the HPLC analysis of the yeast extract, a peak was eluted at the same retention time as the standard β-carotene. The peak was recovered and its absorbance spectrum was analyzed to confirm it to be β-carotene. Lycopene was detected and identified in the yeast extract in a similar way. The yield of β-carotene was 91 μg per g dry weight of the cells.

In another experiment, BCAR1 was further transformed with a plasmid vector pTRP56 (Clontech), which has the TRP1 gene, by the lithium method, and transformants were selected on a medium without leucine and tryptophane to obtain a yeast transformant BCAR2. BCAR2 was examined for its β-carotene production in the same way as for BCAR1 except that the medium was devoid of tryptophane. BCAR2 produced β-carotene at a yield about 1.2 times higher than BCAR1.

Deposition of Microorganism

Microorganism relating to the present invention is deposited at Fermentation Research Institute, Japan as follows:

| Microorganism | Accession number | Date of deposit |
|---|---|---|
| *Escherichia coli* | FERM BP 2377 | April 11, 1989 |

What is claimed is:

1. A process for producing a carotenoid or a precursor compound which is selected from the group consisting of geranylgeranyl pyrophosphate, phytoene, lycopene, β-carotene, zeaxanthin-diglucoside, which comprises transforming a host with at least one of the DNA sequences selected from the group consisting of:

- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1;
- a DNA sequence encoding a polypeptide which has an enzymatic activity for converting zeaxanthin into zeaxanthin-diglucoside and whose amino acid sequence consists of the amino acid sequence of SEQ ID NO: 2;
- a DNA sequence encoding a polypeptide which has an enzymatic activity for converting lycopene into β-carotene and whose amino sequence consists of the amino acid sequence of SEQ ID NO: 3;
- a DNA sequence encoding a polypeptide which has an enzymatic activity for converting phytoene into lycopene and whose amino acid sequence consists of the amino acid sequence of SEQ ID NO: 4;
- a DNA sequence encoding a polypeptide which has an enzymatic activity for converting geranylgeranyl pyrophosphate into phytoene and whose amino acid sequence consists of the amino acid sequence of SEQ ID NO: 5; and
- a DNA sequence encoding a polypeptide which has an enzymatic activity for converting β-carotene into zeaxanthin and whose areinc acid sequence consists of the areinc acid sequence of SEQ ID NO: 6;

culturing the transformant and
expressing the DNA sequences by the culture, wherein, the host is *Escherichia coli*, *Zymomonas mobilis*, or *Saccharomyces cerevisiae*.

2. The process according to claim 1, wherein said compound is geranylgeranyl pyrophosphate and said at least one of the DNA sequences is the following DNA sequence:
- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1.

3. The process according to claim 1 wherein said compound is phytoene and said at least one of the DNA sequences is the following DNA sequences:
- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1; and
- a DNA sequence encoding a polypeptide which has an enzymatic activity for converting geranylgeranyl pyrophosphate into phytoene and whose amino acid sequence consists of the amino acid sequence of SEQ ID NO: 5.

4. The process according to claim 1 wherein said compound is lycopene and said at least one of the DNA sequences is the following DNA sequences:
- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1;
- a DNA sequence encoding a polypeptide which has an enzymatic activity for converting phytoene into lycopene and whose amino acid sequence consists of the amino acid sequence of SEQ ID NO: 4; and
- a DNA sequence encoding a polypeptide which has an enzymatic activity for converting geranylgeranyl pyrophosphate into phytoene and whose amino acid sequence consists of the amino acid sequence of SEQ ID NO: 5.

5. The process according to claim 1, wherein said compound is β-carotene and said at least one of the DNA sequences is the following DNA sequences:
- a DNA sequence encoding a polypeptide which has an enzymatic activity for converting farnesyl pyrophosphate into geranylgeranyl pyrophosphate and whose amino acid sequence consists of the amino sequence of SEQ ID NO: 1;
- a DNA sequence encoding a polypeptide which has an enzymatic activity for converting lycopene into β-carotene and whose amino acid sequence consists of the amino acid sequence of SEQ ID NO:3;
- a DNA sequence encoding a polypeptide which has an enzymatic activity for converting phytoene into lycopene and whose amino acid sequence consists of the amino acid sequence of SEQ ID NO:4; and
- a DNA sequence encoding a polypeptide which has an enzymatic activity for converting geranylgeranyl pyrophosphate into phytoene and whose amino acid sequence consists of the amino acid sequence of SEQ ID NO: 5.

6. The process according to claim 1 wherein said compound is zeaxanthin and said at least one of the following DNA sequences is the DNA sequences:
- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1;
- a DNA sequence encoding a polypeptide which has an enzymatic activity for converting lycopene into β-carotene and whose amino acid sequence consists of the amino acid sequence of SEQ ID NO:3;
- a DNA sequence encoding a polypeptide which has an enzymatic activity for converting phytoene into lycopene and whose amino acid sequence consists of the amino acid sequence of SEQ ID NO: 4;
- a DNA sequence encoding a polypeptide which has an enzymatic activity for converting geranylgeranyl pyrophosphate into phytoene and whose amino acid sequence consists of the amino acid sequence of SEQ ID NO: 5; and
- a DNA sequence encoding a polypeptide which has an enzymatic activity for converting β-carotene into zeaxanthin and whose amino acid sequence consists of the amino acid sequence of SEQ ID NO: 6.

7. The process according to claim 1 wherein said compound is zeaxanthin-diglucoside and said at least one of the DNA sequences is the following DNA sequences:
- a DNA sequence encoding a polypeptide which has an enzymatic activity for converting farnesyl pyrophosphate into geranylgeranyl pyrophosphate and whose amino acid sequence consists of the amino acid sequence of SEQ ID NO: 1;
- a DNA sequence encoding a polypeptide which has an enzymatic activity for converting zeaxanthin into zeaxanthin-diglucoside and whose amino acid sequence consists of the amino acid sequence of SEQ ID NO: 2;
- a DNA sequence encoding a polypeptide which has an enzymatic activity for converting lycopene into β-carotene and whose amino acid sequence consists of the amino acid sequence of SEQ ID NO:3;
- a DNA sequence encoding a polypeptide which has an enzymatic activity for converting phytoene into lycopene and whose amino acid sequence consists of the amino acid sequence of SEQ ID NO: 4;
- a DNA sequence encoding a polypeptide which has an enzymatic activity for converting geranylgeranyl pyrophosphate into phytoene and whose amino acid sequence consists of the amino acid sequence of SEQ ID NO:5; and
- a DNA sequence encoding a polypeptide which has an enzymatic activity for converting β-carotene into zeaxanthin and whose amino acid sequence consists of the amino acid sequence of SEQ ID NO:6.

8. The process according to claim 1 wherein said compound is lycopene and said at least one of the DNA sequences is the following DNA sequences:
- a DNA sequence encoding a polypeptide which has an enzymatic activity for converting phytoene into lycopene and whose amino acid sequence consists of the amino acid sequences of SEQ ID NO: 4; and
- a DNA sequence encoding a polypeptide which has an enzymatic activity for converting geranylgeranyl pyrophosphate into phytoene and whose amino acid sequence consist of the amino acid sequence of SEQ ID NO: 5.

9. The process according to claim 1 wherein said compound is β-carotene and said at least one of the DNA sequences is the following DNA sequences:
- a DNA sequence encoding a polypeptide which has an enzymatic activity for converting lycopene into β-carotene and whose amino acid sequence consists of the amino acid sequence of SEQ ID NO:3;

a DNA sequence encoding a polypeptide which has an enzymatic activity for converting phytoene into lycopene and whose amino acid sequence consists of the amino acid sequence of SEQ ID NO:4; and a DNA sequence encoding a polypeptide which has an enzymatic activity for converting geranylgeranyl pyrophosphate into phytoene and whose amino acid sequence consists of the amino acid sequence of SEQ ID NO: 5.

10. The process according to claim 1 wherein said compound is zeaxanthin and said at least one of the DNA sequences is the following DNA sequences:

a DNA sequence encoding a polypeptide which has an enzymatic activity for converting lycopene into β-carotene and whose amino acid sequence consists of the amino acid sequence of SEQ ID NO:3;

a DNA sequence encoding a polypeptide which has an enzymatic activity for converting phytoene into lycopene and whose amino acid sequence consists of the amino acid sequence of SEQ in NO:4;

a DNA sequence encoding a polypeptide which has an enzymatic activity for converting geranylgeranyl pyrophosphate into phytoene and whose amino acid sequence consists of the amino acid sequence of SEQ ID NO:5; and a DNA sequence encoding a polypeptide which has an enzymatic activity for converting β-carotene into zeaxanthin and whose amino acid sequence consists of the amino acid sequence of SEQ ID NO:6.

11. The process according to claim 1 wherein said compound is zeaxanthin-diglucoside and said at least one of the DNA sequences is the following DNA sequences:

a DNA sequence encoding a polypeptide which has an enzymatic activity for converting zeaxanthin into zeaxanthin-diglucoside and whose amino sequence consists of the amino acid sequence of SEQ ID NO:2;

a DNA sequence encoding a polypeptide which has an enzymatic activity for converting lycopene into β-carotene and whose amino acid sequence consists of the amino acid sequence of SEQ ID NO:3;

a DNA sequence encoding a polypeptide which has an enzymatic activity for converting phytoene into lycopene and whose amino acid sequence consists of the amino acid sequence of SEQ ID NO:4;

a DNA sequence encoding a polypeptide which has an enzymatic activity for converting geranylgeranyl pyrophosphate into phytoene and whose amino acid sequence consists of the amino acid sequence of SEQ ID NO:5 and a DNA sequence encoding a polypeptide which has an enzymatic activity for converting β-carotene into zeaxanthin and whose amino acid sequence consists of the amino acid sequence of SEQ ID NO:6.

* * * * *